(12) United States Patent
Saab et al.

(10) Patent No.: US 10,716,891 B2
(45) Date of Patent: Jul. 21, 2020

(54) IMPLANTABLE FLUID DELIVERY SYSTEM

(71) Applicant: Ihab Saab, Detroit, MI (US)

(72) Inventors: Ihab Saab, Detroit, MI (US); Nathan Waters, Negaunee, MI (US); Michael E. Neal, Holly, MI (US); Joel Carne, Holly, MI (US); Lanie R. Belloli, Almont, MI (US); Massoud S. Tavakoli, Flint, MI (US)

(73) Assignee: ISaab Innovations LLC, Troy, MI (US)

( * ) Notice: Subject to any disclaimer, the term of this patent is extended or adjusted under 35 U.S.C. 154(b) by 242 days.

(21) Appl. No.: 15/565,051

(22) PCT Filed: Apr. 5, 2016

(86) PCT No.: PCT/US2016/026016
§ 371 (c)(1),
(2) Date: Oct. 6, 2017

(87) PCT Pub. No.: WO2016/164349
PCT Pub. Date: Oct. 13, 2016

(65) Prior Publication Data
US 2018/0110919 A1 Apr. 26, 2018

Related U.S. Application Data

(60) Provisional application No. 62/144,022, filed on Apr. 7, 2015.

(51) Int. Cl.
*A61M 5/142* (2006.01)
*A61M 5/168* (2006.01)
*A61M 5/172* (2006.01)
*A61M 39/02* (2006.01)
*A61M 5/14* (2006.01)

(52) U.S. Cl.
CPC .... *A61M 5/14276* (2013.01); *A61M 5/16804* (2013.01); *A61M 5/16881* (2013.01);
(Continued)

(58) Field of Classification Search
CPC .......... A61M 5/14276; A61M 39/0208; A61M 2039/0211; A61M 2039/0276;
(Continued)

(56) References Cited

U.S. PATENT DOCUMENTS

| 4,816,016 A | 3/1989 | Schulte et al. |
| 5,823,991 A * | 10/1998 | Shim ........................ A61F 5/41 604/500 |

(Continued)

FOREIGN PATENT DOCUMENTS

EP  2832390  2/2015

OTHER PUBLICATIONS

International Search Report for PCT/US2016/26016, Completed by the U.S. Patent and Trademark Office on Oct. 20, 2016, 5 Pages.

*Primary Examiner* — Emily L Schmidt
(74) *Attorney, Agent, or Firm* — Brooks Kushman P.C.

(57) ABSTRACT

An implantable system for delivering fluids, such as drugs, to one or more anatomical structures in a patient's (i.e., human or animal) body. A number of medical conditions require continual and/or periodic administration of fluids (e.g., drugs) to target regions (e.g., anatomic organs) of the body. Accessibility to those target regions might be limited technically for ex. and not limited to: frequent endoscopic, radiologically guided or surgical approaches. The system delivers the fluid needed in a continual or intermittent fashion to the target region. It controls the amount of fluid delivered to the target region and measures the intended physiologic effect of the fluid delivered.

18 Claims, 11 Drawing Sheets

(52) U.S. Cl.
CPC ...... *A61M 5/1723* (2013.01); *A61M 39/0208* (2013.01); *A61M 2005/1406* (2013.01); *A61M 2205/3507* (2013.01); *A61M 2205/50* (2013.01); *A61M 2205/82* (2013.01)

(58) Field of Classification Search
CPC .. A61M 2039/0282; A61M 2039/0255; A61M 2039/0214; A61M 2039/0217; A61F 2/26
See application file for complete search history.

(56) References Cited

U.S. PATENT DOCUMENTS

| | | | |
|---|---|---|---|
| 6,929,631 B1* | 8/2005 | Brugger | A61M 39/0208 604/247 |
| 7,713,251 B2 | 5/2010 | Tallarida et al. | |
| 7,803,143 B2 | 9/2010 | Tallarida et al. | |
| 8,034,029 B2 | 10/2011 | Steinbach et al. | |
| 8,603,051 B2 | 12/2013 | Kuo et al. | |
| 2003/0014014 A1 | 1/2003 | Nitzan | |
| 2004/0059285 A1* | 3/2004 | Mathiesen | A61N 1/08 604/65 |
| 2004/0220553 A1 | 11/2004 | Olsen | |
| 2006/0253076 A1 | 11/2006 | Butts et al. | |
| 2007/0233019 A1* | 10/2007 | Forsell | A61M 5/14276 604/288.03 |
| 2009/0227989 A1 | 9/2009 | Burke et al. | |
| 2011/0196198 A1* | 8/2011 | Forsell | A61F 2/26 600/38 |
| 2012/0302959 A1 | 11/2012 | Fielder et al. | |
| 2012/0330235 A1 | 12/2012 | Moga et al. | |
| 2015/0018799 A1 | 1/2015 | Lewis et al. | |

\* cited by examiner

IMPLANTABLE FLUID DELIVERY SYSTEM

CROSS-REFERENCE TO RELATED APPLICATION

This application is the U.S. national phase of PCT Application No. PCT/US2016/026016 filed on Apr. 5, 2016, which claims the benefit of U.S. Provisional Patent Application No. 62/144,022 filed on Apr. 7, 2015, the disclosures of which are incorporated in their entirety by reference herein.

This is a new international application under the Patent Cooperation Treaty (PCT).

TECHNICAL FIELD

The present invention is generally related to implantable medical devices and, more particularly, to an implantable system for delivering fluids, such as drugs, to one or more anatomical structures in a patient's (i.e., human or animal) body.

BACKGROUND

A number of medical conditions require continual and/or periodic administration of fluids (e.g., drugs) to target regions (e.g., anatomical structures) of the body. A variety of implantable fluid delivery devices/systems are known and generally include a port having a reservoir with a catheter attached thereto. Fluid in the reservoir of the implanted port is pumped by one or more pumps through the catheter and to the target region(s) of the body. The port is implanted beneath the skin of the patient and may include a septum that is penetrable by a hypodermic needle. Thus, conventional injections of a medication into a patient having an implanted port are made by inserting a needle through the patient's skin and through the septum in the port. Fluid is injected through the needle and into the reservoir of the port where it passes into the catheter and eventually out to the target region(s).

BRIEF DESCRIPTION OF THE DRAWINGS

One or more embodiments of the invention will hereinafter be described in conjunction with the appended drawings, wherein like designations denote the same or similar elements, and wherein.

DETAILED DESCRIPTION OF ILLUSTRATED EMBODIMENT(S)

The description below pertains to an implantable fluid delivery system that includes a port, for example, a port that may be implanted subcutaneously, configured to deliver a fluid, generally a drug, to one or more implantable pods located or disposed at or on one or more target anatomical structures (e.g., pylorus, bladder, etc.). An example of a fluid that may be delivered using the system and method described herein is botulinum toxin or botox; though it will be appreciated that the system and method may be utilized to deliver any number of other fluids, and therefore, the present disclosure is not intended to be limited to the use of any particular fluid(s). It will be further appreciated that the system may be used to treat any number of diseases or conditions in which fluid has to be delivered (e.g., injected into) one or more anatomical structures and/or one or more locations or regions of an anatomical structure. These diseases/conditions may include, but are certainly not limited to, bladder and urethral dysfunction, overactive bladder syndrome, benign prostatic hyperplasia, painful bladder syndrome/interstitial cystitis, achalasia, and obesity to cite only a few possibilities. Accordingly, it will be appreciated that use of the system described herein is not intended to be limited to the treatment of any particular disease(s)/condition(s), and/or to the implantation of the devices of the system at any particular location(s) within a patient's anatomy.

Figure 1:
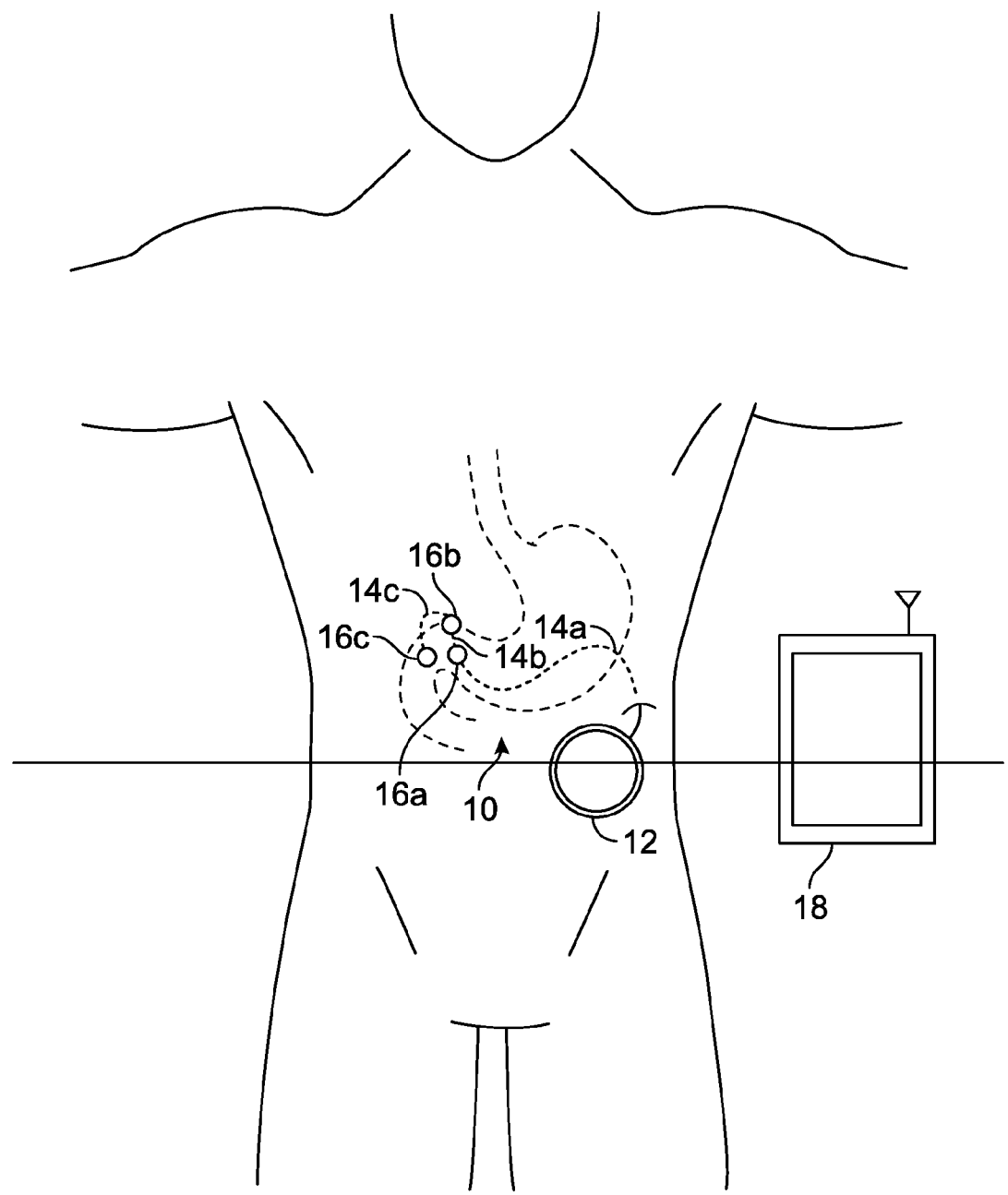
FIG. 1 is a diagrammatic view of an illustrative embodiment of a fluid delivery system.

With reference to FIG. 1, there is shown a diagrammatic representation of a fluid delivery system 10 implanted within the body of a patient, in this case, the body of a human being. According to an embodiment, the fluid delivery system 10 (hereinafter "system 10") generally includes a port 12, one or more catheters 14, and one or more implantable pods 16. As will be described in greater detail below, at least one of the catheters 14 (catheter 14a in FIG. 1) is configured to couple (e.g., fluidly, electrically, etc.) the port 12 to at least one of the pods 16 (pod 16a in FIG. 1), while one or more other of the catheters 14 (if applicable) are configured to couple two adjacent pods 16 together and to facilitate fluid communication and, in at least some embodiments, electrical connection/communication, therebetween (e.g., catheter 14b couples pod 16a to pod 16b, and catheter 14c couples pod 16b to pod 16c). In at least some embodiments, the system 10 may include additional components, for example and without limitation, an interrogator 18 or other base station configured to communicate with electronics housed within the port 12 and/or pod(s) 16. In other embodiments, however, that or those additional components may be separate and distinct from the system 10 but may be used in conjunction therewith.

Figure 2:
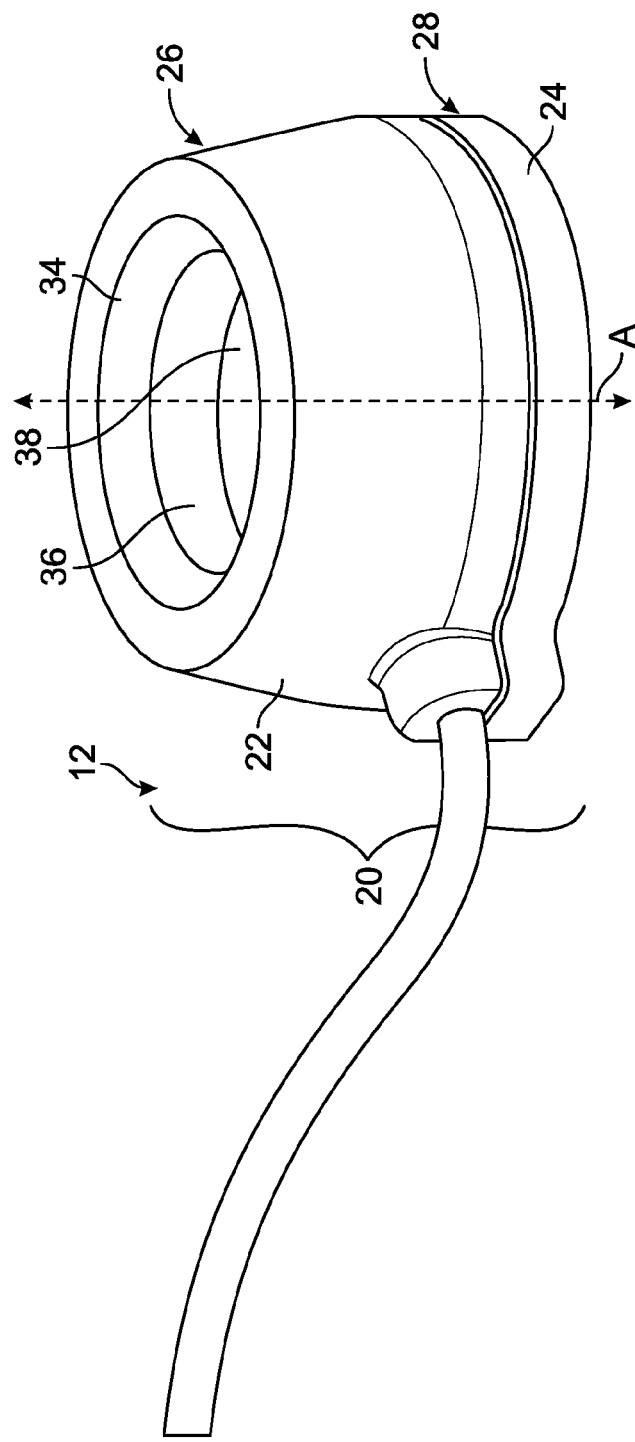
FIG. 2 is an isometric view of an illustrative embodiment of a port of the fluid delivery system illustrated in FIG. 1.

In an embodiment, the port 12 may be an implantable port configured to be implanted underneath the surface of the skin and to be held in place by, for example, suturing the port 12 to a muscle wall or another anatomical structure beneath the surface of the skin. As illustrated in, for example, FIGS. 2 and 4, the port 12 generally comprises a body 20 that, in an embodiment, includes a first portion 22 and a second portion 24, and includes or defines a central axis A. The first and second portions 22, 24 may be integrally formed so as to form a single piece, or, alternatively, may comprise separate pieces that are operatively coupled together (i.e., directly coupled or indirectly coupled via intervening component(s) using techniques well-known in the art (e.g., friction or interference fit connections, threaded connections, mechanical fasteners, and/or adhesives, to cite just a few possibilities).

In an embodiment, the first portion 22 of the port 12 has a first end 26 and a second end 28 opposite the first end 26. The first portion 22 further includes an opening 30 at a first end 26 providing access to a fluid reservoir 32 disposed within the first portion 22. In an embodiment, the port 12 includes a diaphragm or septum 34 that is carried by the body 20 (e.g., the first portion 22 of the body 20) and that extends across and overlays the opening 30. The septum 34 is penetrable by a needle of or carried by a syringe to fill the reservoir 32 with fluid that is to be delivered to the pod(s) 16. In an embodiment, the septum 34 may comprise a silicon membrane; though in other embodiments the septum 34 may take other forms. The septum 34 may be coupled to the first port 22 in a number of ways. One way comprises affixing the septum 34 to an affixation surface (not shown), which may be an axially-facing surface that faces away from the body 20 of the port 12, using a suitable adhesive. In another embodiment, the septum 34 may be coupled to the port as part of the molding process used to form or construct the port 12. In such embodiment, both the periphery of the septum 24 and the affixation surface may be encapsulated in the port 12 during the port manufacturing process. It will be appreciated, however, that other suitable coupling techniques may additionally or alternatively be utilized.

In an embodiment, the reservoir 32 extends from the opening 30 at the first end 26 of the first portion 22 to an intermediate point between the first and second ends 26, 28 of the first portion 22, and may be defined or bounded by one or more walls. For example, in the embodiment illustrated in FIGS. 2 and 3, the reservoir 32 may include one or more side walls 36 extending axially from the opening 30 (or in close proximity thereto) to a bottom wall 38. In another embodiment, such as, for example, that illustrated in FIG. 4, the reservoir 32 may have a substantially funnel or conical shape having one or more side walls 36 extending both axially and radially-inward from the opening 30 to a point or bottom wall located between the first and second ends 26, 28 of the first portion 22. Accordingly, it will be appreciated that the reservoir 32 is not limited to any particular configuration(s), but rather any suitable configuration may be utilized.

Figure 3:
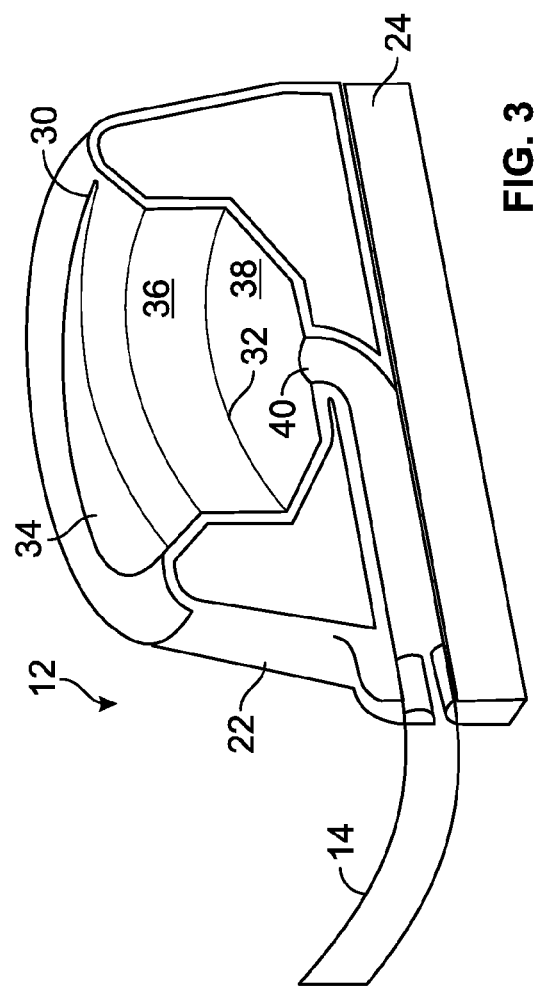
FIG. 3 is an isometric cross section view of the port illustrated in FIG. 2, taken along the lines 3-3 in FIG. 2.
Figure 6:
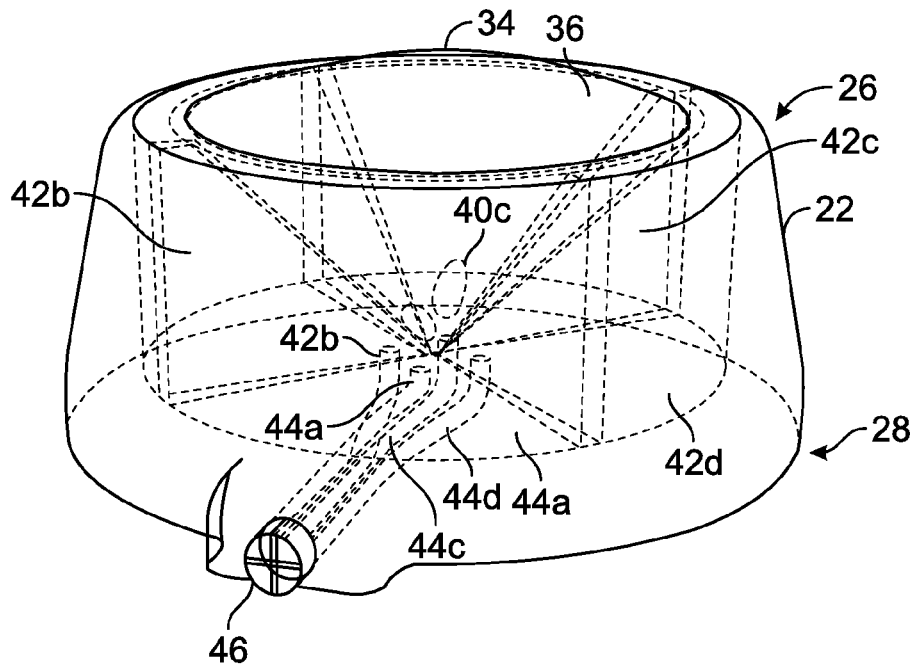
FIG. 6 is an isometric view of a first or top portion of the port illustrated in FIG. 4.
Figure 7:
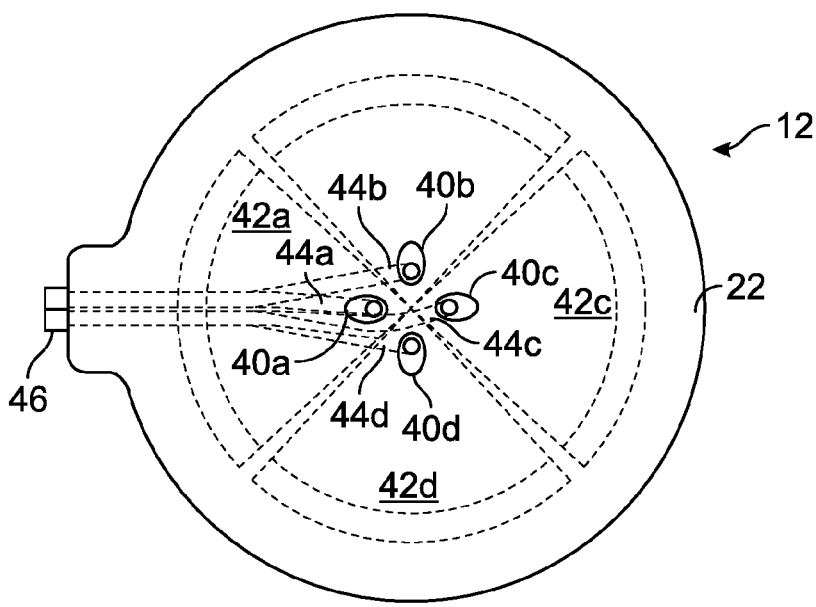
FIG. 7 is a top plan view of the port illustrated in FIG. 4.

The port 12 may include one or more fluid passageways 40 in fluid communication with the reservoir to allow fluid to flow out of the reservoir 32. The passageway(s) 40 may extend from the bottom of the reservoir 32 (e.g., from a bottom wall of the reservoir 32 (as shown in FIG. 3)) or from a sidewall (as shown in, for example, FIGS. 6 and 7), though other configurations and arrangements are certainly possible. In an embodiment such as that illustrated in FIGS. 2 and 3, the passageways(s) 40 fluidly couple the reservoir 32 to the catheter 14 that, in turn, couples the port 12 with one or more of the pods 16.

In other embodiments such as, for example, that illustrated in FIGS. 4-7, the passageway(s) 40 fluidly couple the reservoir 32 to one or more chambers 4 (e.g., a plurality of chambers) disposed in the first portion 22 of the port 12. In such an embodiment, fluid flows from the reservoir 32 to the chamber 42 before flowing to the catheter 14. By way of illustration, the first portion 22 of the port 12 may include a plurality of chambers 42, for example and as illustrated in FIGS. 4-7, four (4) chambers 42 (i.e., chambers 42a, 42b, 42c, and 42d), each corresponding to one or more pods 16 of the system 10. It will be appreciated that while the illustrated embodiment includes four (4) chambers, in other embodiments, the port 12 may include more or fewer than four (4) chambers. Accordingly, the present disclosure is not limited to the port 12 including any particular number of chambers. In any event, because the port 12 in the embodiment illustrated in FIGS. 4-7 includes four (4) chambers, the port 12 includes four (4) passageways 40 (40a, 40b, 40c, and 40d shown in FIG. 7, for example), each of which is configured to allow fluid in the reservoir 32 to flow into a respective chamber 42. In an embodiment, and as shown schematically in FIG. 4 for one fluid passageway 40, the fluid passageways 40 either comprise or have disposed therein, one-way valves 41 to allow fluid to flow from the reservoir 32 to the chambers 42, but to prevent the flow of fluid in the opposite direction. In such an embodiment, any suitable one-way valve may be used, as the present disclosure is not intended to be limited to any particular type(s).

Each chamber 42 may be defined or bounded by one or more interior walls of the first portion 22, and may be coupled with one or more drains 44 in the port 12 to allow fluid to flow out from the chamber 42. Accordingly, in an embodiment such as that illustrated in FIGS. 6 and 7 wherein the port 12 includes four (4) chambers 42 (i.e., chambers 42a-42d), there may be four (4) drains 44 (i.e., drains 44a-44d). Each drain 44 may extend from the corresponding chamber 42 to a connector member or element 46 carried in or by the first portion 22 of the port 12 that is configured to mate with the end of the catheter 14 (e.g., a complementary connector member at the end of the catheter 14), and that allows fluid to flow from the port 12 to the catheter 14. The drain(s) 44 may be arranged in such a manner that when the catheter 14 is coupled or connected to the port 12, each drain 44 is aligned with a corresponding lumen of or in the catheter 14. The connector member 46 may comprise a male or female connector member, and may comprise any suitable connector known in the art that will facilitate the passage of fluid from the port 12 to the catheter 14. As such, the present disclosure is not limited to any particular type(s) of connector members or connection techniques.

Figure 5:
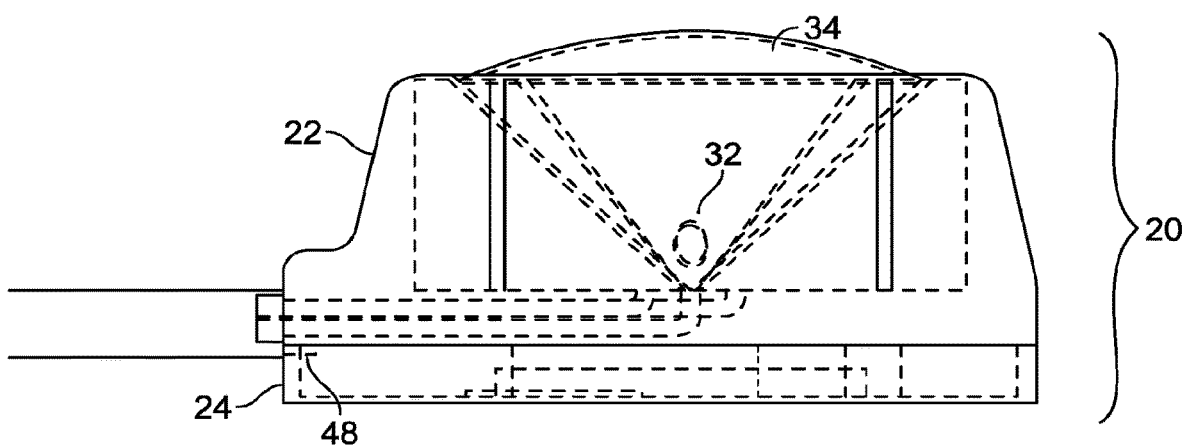
FIG. 5 is a side elevation view of the port illustrated in FIG. 4.
Figure 8:
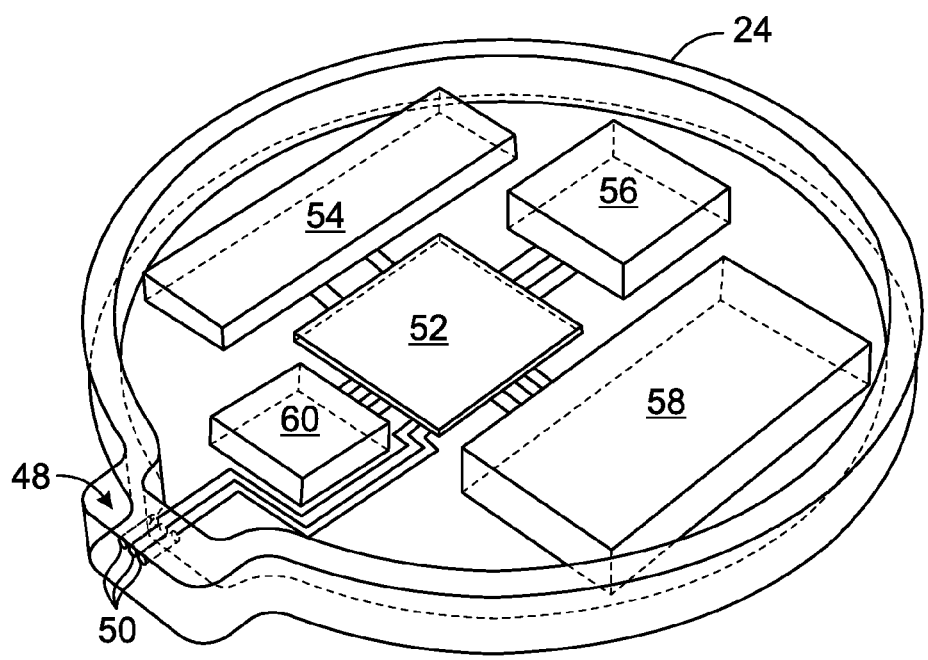
FIG. 8 is an isometric view of an illustrative embodiment of a bottom or base portion of the ports illustrated in FIGS. 2 and 4.

With reference to FIGS. 5 and 8, the second portion 24 of the port body 20 is configured to house various electronics used in the control and operation of the system 10. In an embodiment, the port 12 also includes an electromechanical connector 48 that is carried by the second portion 24 and that is comprised of one or more electrical contacts 50 to allow the port 12, and the electronics stored therein, in particular, to be electrically connected to the pod(s) 16. Any number of electrical components may be housed within the second portion 24, including, but not limited to, one or more of an electronic control unit (ECU) 52, a power source 54, a transmitter/receiver (e.g., a transceiver) 56, an ohm meter 58, one or more switches or switch arrays, and various conductors or wires to allow each the components to be connected to each other and/or to the electrical contacts 50 of the electromechanical port 48.

The ECU 52 may include any variety of electronic processing devices, memory devices, input/output (I/O) devices, and/or other known components, and may perform various functions relating to, for example, the operation and control of the system 10. In an illustrative embodiment, the ECU 52 comprises an electronic memory device and an electronic processing device. The electronic memory device is configured to store various information, instructions, software, algorithms, data, threshold values, etc. to be used in the control and operation of the system 10. The electronic processing device, which may comprise, for example, and without limitation, a microprocessor, a microcontroller, an application specific integrated circuit (ASIC), etc., is configured to execute instructions for software, firmware, programs, algorithms, scripts, etc. that are stored in the memory device of the ECU 52, and may at least partially govern some or all of the processes and methods described herein.

The power source 54 may comprise one or more batteries or any other suitable power source known in the art, and may serve a number of purposes. For instance, it may provide operating power to other components housed within the second portion 24 of the port 12, and/or to components or devices located in the pod(s) 16 of the system 10. The power source 54 may also be used to facilitate impedance measurements of tissue proximate one or more of the pod(s) 16. Accordingly, the power source 54 may take any number of forms and may serve any number of purposes, including purposes not expressly described herein.

The transmitter/receiver 56 may comprise a combined transmitter/receiver (i.e., a transceiver), or may comprise a transmitter and a separate receiver. In either instance, the structure and function of the transmitter/receiver 56 is well known in the art, and as such, a detailed description will not be provided. To summarize, however, the transmitter/receiver 56 may comprise any suitable transmitter/receiver known in the art capable of receiving and transmitting electrical signals, for example, radio frequency (RF) signals. To that end, the transmitter/receiver 56 may include an antenna and other components required for receiving and transmitting electrical signals in the manner required for operating the system 10. The transmitter/receiver 56 may be configured to facilitate wireless communications between the port 12 (and the ECU 52 thereof, in particular) and one or more other components of the system 10, and/or between the port 12 and one or more other components or devices that are not part of the system 10, but that are nonetheless used in conjunction with the system 10. For example, the transmitter/receiver 56 may be configured to receive instructions, commands, and/or information from, and/or to send instructions, commands, and/or information to, an interrogator (the interrogator 18 described below) or another components (e.g., base station) located, for example, at a patient's bedside. In at least certain embodiments, the transmitter/receiver 56 may be additionally or alternatively configured to receive, for example, readings from wireless sensors (e.g., flow sensors) located in the pod(s) 14 of the system 10. In any event, in an embodiment, the transmitter/receiver 56 is electrically connected to the ECU 52 so as to allow for data and other information to be passed to and from the ECU 52. Again, it will be appreciated that any suitable type of transmitter/receiver may be used, as the present disclosure is not limited to any particular type of transmitter/receiver.

As is well-known in the art, the ohmmeter 58 is configured and operable to measure electrical resistance or impedance. As will be described in greater detail below, the ohmmeter 58 is configured to measure the electrical resistance or impedance between two or more of the pods 16, which, in an embodiment, comprises the resistance or impedance of tissue proximate two or more of the pods 16. While in an embodiment the port 12, and thus the system 10, includes an ohmmeter that is separate and distinct from the ECU 52, in other embodiments, the functionality of the ohmmeter 58 may be integrated within the functionality of the ECU 52, and thus, the ECU 52 comprises the ohmmeter 58. Accordingly, it will be appreciated that any number of configurations or arrangements of the ohmmeter 58 may be utilized.

As briefly described above, in addition to the components described above, one or more switches 60 or arrays of switches 60 may also be housed in the second portion 24 of the port 12. As will be described in greater detail below, some or all of these switches 60 may be used to electrically connect certain electronics or electrical components in the port 12 with one or more components in the pods 16. For example, a switch 60 may be configured to electrically connect the power source 54 to a fluid control valve located in a pod 16. Another switch 60 may be configured to electrical connect the power source 54 to a needle actuation mechanism (e.g., electromagnet(s), piezoelectric element(s), etc.) located in a pod 16. Switches may also be used to electrically connect electrodes (e.g., needles) in the pods 16 to, for example, the ohmmeter 58 or ECU 52, and/or sensors (e.g., flow sensors) in the pods 16 to the ECU 52. In any event, operation of the switches 60 may be controlled by the ECU 52 such that the ECU 52 may command the opening and closing of the switches. Additionally, the switches 60 may comprise any suitable type of switch, for example, solid state switches and/or electromechanical switches, the operation of which is/are well known in the art. Accordingly, it will be appreciated that any number of switches 60 may be provided to selectively connect various components of the port 12 and pods 16 together, and that different types of suitable switches may be used.

The electromechanical port 48 in or carried by the body 20 of the port 12 may comprise any suitable electromechanical connector known in the art, and is configured to be mated with a complementary electromechanical connector of the catheter 14. As shown in FIG. 8, the electromechanical connector 48 may comprise a female connector such that it is adapted to receive a complementary male connector of the catheter 14, or may comprise a male connector configured to be inserted or plugged into a female connector of the catheter 14. Accordingly, the present disclosure is not limited to the use of any particular type of electromechanical connector, but rather any suitable connector may be used.

As briefly described above, the system 10 includes one or more catheters 14. In an embodiment wherein the system 10 includes a single pod 16, the system 10 may include a single catheter 14 for coupling the port 12 with the pod 16 and for facilitating fluid communication and/or electrical connection(s) therebetween. However, in an embodiment wherein the system 10 includes a plurality of pods, a plurality of catheters 14 may be provided. For example, in the embodiment illustrated in FIG. 1 wherein the system 10 includes three (3) pods 16a-16c, the system includes three (3) catheters 14-catheter 14a coupling the port 12 to the first pod 16a, catheter 14b coupling the first pod 16a to the second pod 16b, and catheter 14c coupling the second pod 16b to the third pod 16c. Accordingly, the number of catheters 14 included in the system 10 may be dependent, at least in part, on the number of pods 16 included in the system 10.

Figure 9:
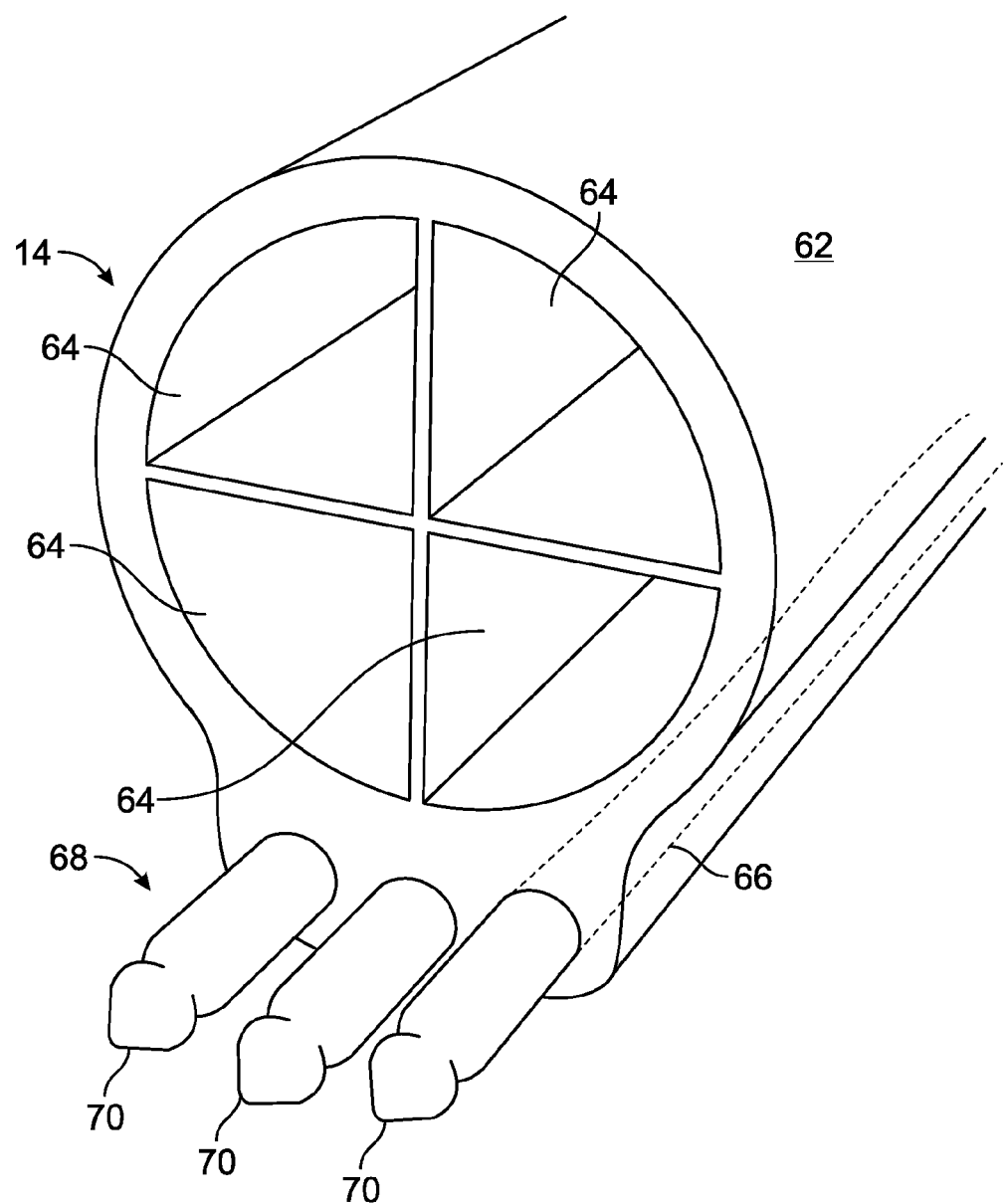
FIG. 9 is an isometric view of a portion of an illustrative embodiment of a catheter of the fluid delivery system illustrated in FIG. 1.

With reference to FIG. 9, each catheter 14 has a shaft 62 having a first end and a second end opposite the first end, and that in an embodiment comprises a flexible shaft. The shaft 62 further includes one or more fluid lumens 64 disposed therein extending between the first and second ends. As shown in FIG. 9, the fluid lumens 64 may be integrally formed into the catheter shaft 62, or alternatively may comprise one or tube(s) that are bundled within with the shaft 62. In either instance, the number of fluid lumens 64 that the catheter 14 includes may be dependent, at least in part, on the number of pods 16 in the system 10, and/or the number of pods 16 downstream from that particular catheter 14. For example, in an embodiment such as that illustrated in FIG. 1 wherein the system 10 includes three (3) pods 16, the shaft 62 of at least the catheter 14a that couples the port 12 to the first pod 16a may include three (3) lumens 64, each one feeding a respective one of pods 16a-16c. In another embodiment, however, the shaft 62 may include a single fluid lumen 64 that feeds all three pods 16a-16c. In such an embodiment, the catheter 14 may include orifices or outlets to which the pods 16a-16c may be coupled and through which fluid flowing through the single lumen 64 may pass to the pods 16a-16c. In other words, the catheter 14 may have a number of branches, each one of which is configured to be coupled to a respective pod 16 to supply fluid thereto. Accordingly, it will be appreciated that the number of lumens 64 that a shaft 62 of a given catheter 14 may have is not limited to any particular number, but rather different catheters 14 may have different numbers of lumens 64.

In addition to the fluid lumen(s) 64, the shaft 62 of a catheter 14 may further include one or more passageways 66 for housing electrical wires or conductors that extend from the first end of the catheter shaft 62 to the second end, and which may be used for electrically connecting electronics or electrical components in the port 12 to various components in the pods 16 (e.g., valves, sensors, needle actuators, etc.). In other embodiments, the conductors/wires may be routed through the catheter(s) 14 in a manner other than through a passageway 66, or even possibly through the fluid lumen(s) 64.

Figure 4:
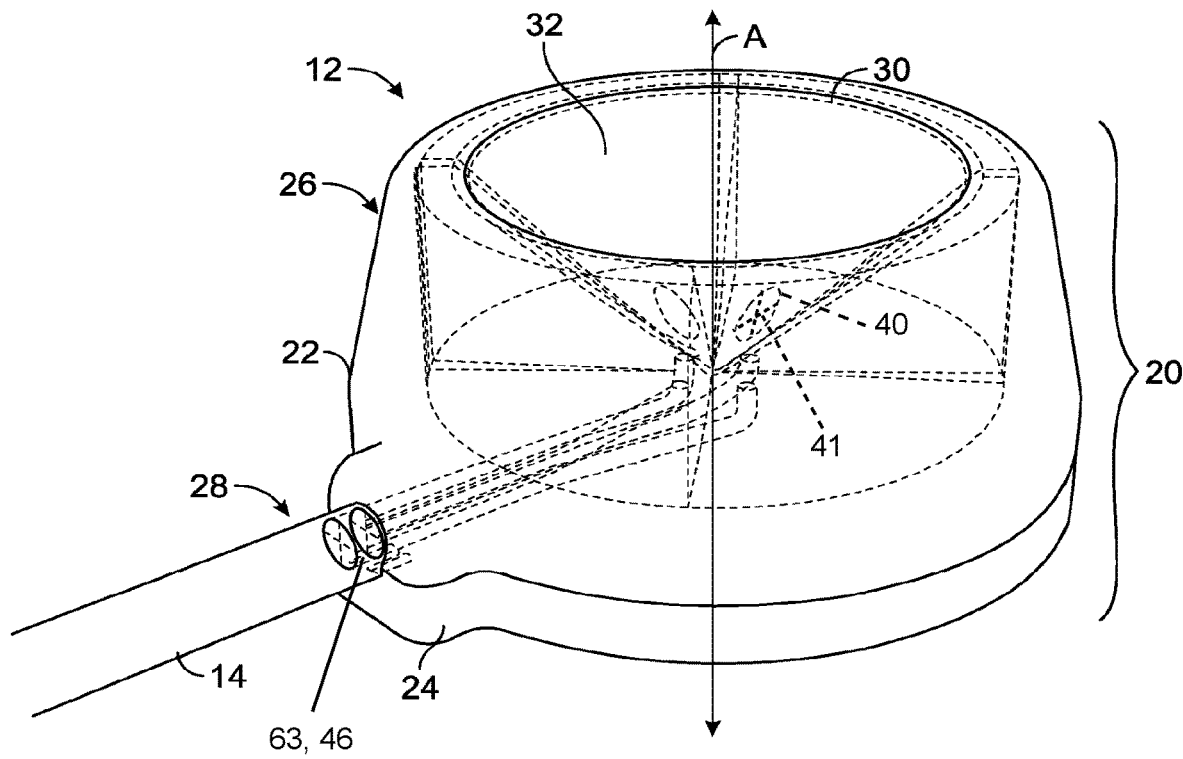
FIG. 4 is an isometric view of another illustrative embodiment of a port of the fluid delivery system illustrated in FIG. 1.
Figure 10A:
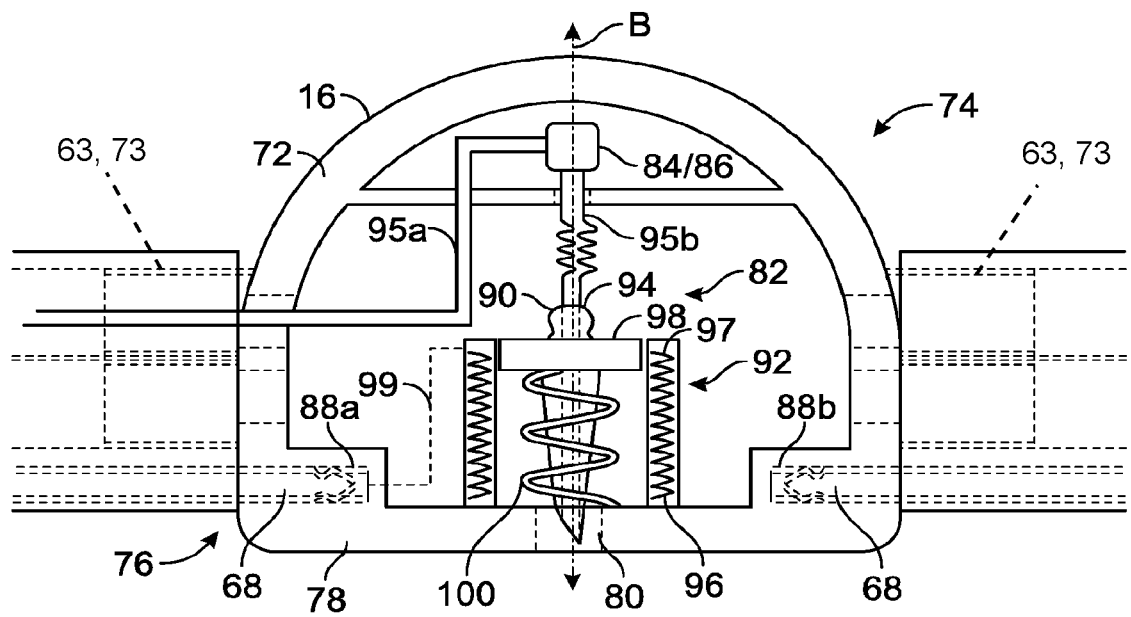
FIGS. 10a and 10b are diagrammatic and side elevation views of an illustrative embodiment of a pod of the fluid delivery system illustrated in FIG. 1, with the needle assembly thereof in a retracted state and a deployed state, respectively.

In any event, the fluid lumens 64 and electrical conductors extending through the shaft 62 of a catheter 14 may each terminate at one or more connectors disposed at either end of the shaft 62. These connectors are configured to couple or connect (e.g., fluidly, electrically, etc.) the catheter 14 between or to the port 12 and a pod 16, or between or to a pair of pods 16 to facilitate fluid and/or electrical communication/connections between the components being coupled together. More particularly, the first and second ends end of a given catheter 14 may include or carry connector 63 that is configured to be mated with a complementary connector of either the port 12 or a pod 16, such as connector 73 of a pod as shown in FIG. 10a or connector 46 of the port 12 as shown in FIG. 4, so as to allow fluid to flow from the port 12 or pod 16 to the catheter 14, or from the catheter 14 to a pod 16, as the case may be. Each end of the given catheter 14 may further include or carry an electromechanical connector 68 configured to be mated with a complementary electromechanical connector of either the port 12 (e.g., electromechanical connector 48) or a pod 16 to electrically connect the electronics or electrical components of the port 12 to the electrical conductors in the catheter 14, or the electrical conductors in the catheter 14 to electrical conductors or components in the pod 16 to which the catheter 14 is being coupled. As shown in FIG. 9, the electromechanical connector 68 on at least one end of one catheter 14 may comprise a male connector that includes a plurality of electrical contacts 70; though it will be appreciated that a female connector configured to receive a complementary male connector may certainly be used instead. In any event, the connectors of the catheter 14 may comprise any suitable connectors known in the art, including, for example, a single connector that facilitates both the electrical connection and fluid communication between the components the catheter 14 is coupling together, as opposed to two separate connectors on one end of the catheter 14. As such, the present disclosure is not limited to any particular type(s) of connectors or connection techniques for the catheters 14.

Figure 12A:
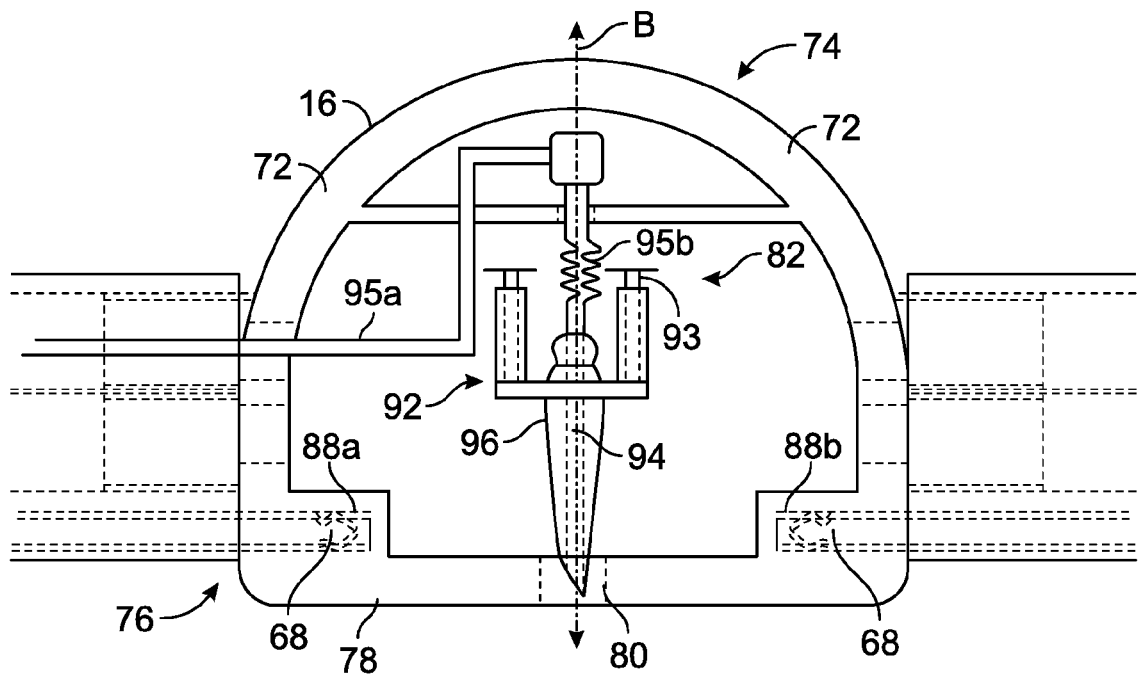
FIGS. 12a and 12b are diagrammatic and side elevation views of yet another illustrative embodiment of a pod of the fluid delivery system illustrated in FIG. 1, with the needle assembly thereof in a retracted state and a deployed state, respectively.
Figure 12B:
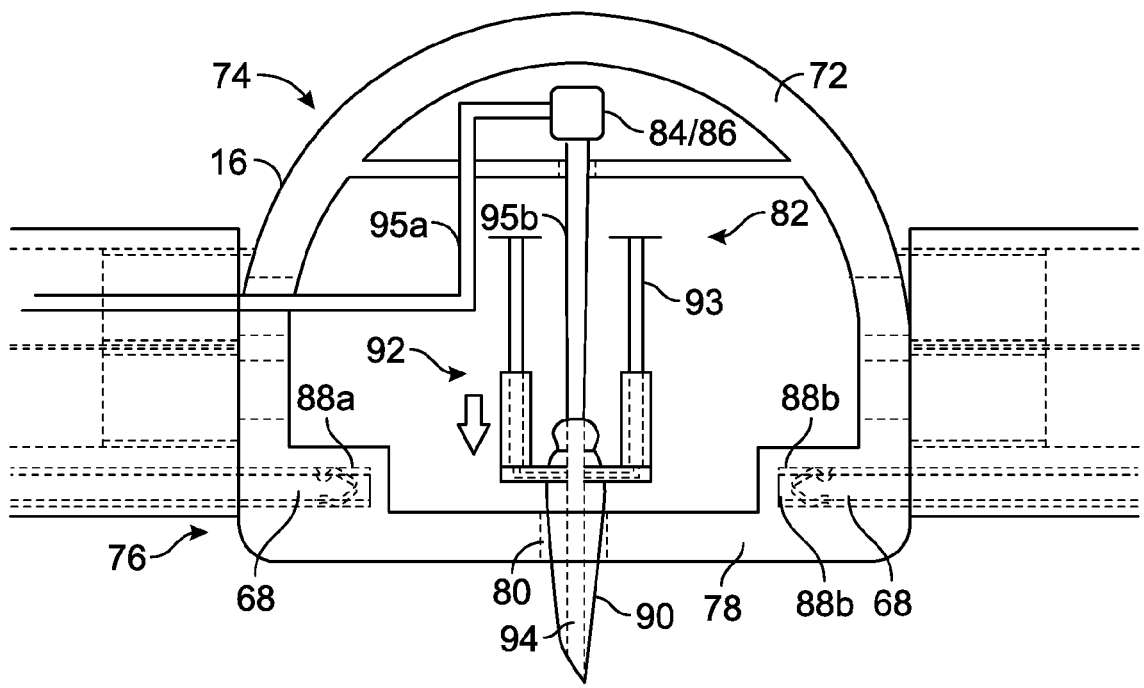
Figure 13:
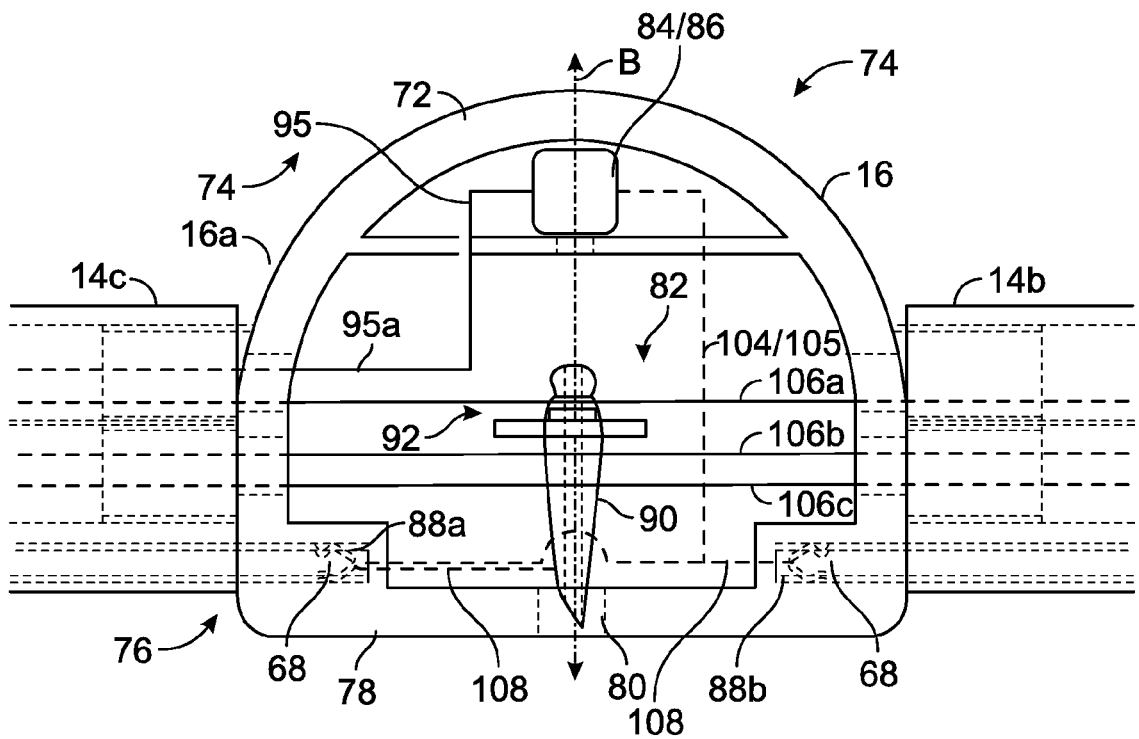
FIG. 13 is a diagrammatic view showing an example of the fluid flow through a pod of the system illustrated in FIG. 1.
Figure 14:
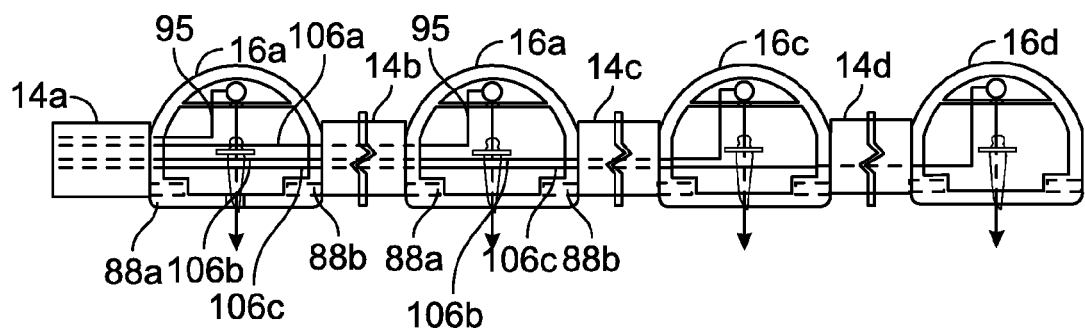
FIG. 14 is a diagrammatic and schematic view of an illustrative arrangement of a plurality of pods of the system illustrated in FIG. 1.

As will be appreciated in view of the foregoing, the system 10 may include one pod 16 or a plurality of pods 16 that may be linked or chained together (see, for example, FIGS. 1 and 14). In either instance, each pod 16 is configured to be implanted in the body of a patient at a particular location at which the delivery of a particular fluid is needed or desired (i.e., at a desired injection site). In an embodiment, the pod 16 may be held in place by suturing the pod 16 to the organ or another anatomical structure to which fluid is being provided. As illustrated in, for example, FIGS. 10a-13, each pod 16 comprises a housing 72 having a first end 74 and a second end 76, and includes or defines an axis B. The housing 72 further includes a base 78 that, for reasons that will become apparent below, includes an axially extending aperture 80 disposed therein. It will be appreciated that unless otherwise noted, the description below of a pod 16 applies with equal weight to each pod 16 of the system 10.

As best shown in FIG. 13, the housing 72 of the pod 16 is configured to house various components of the pod 16, including, for example and without limitation, a deployable needle assembly 82, one or more fluid flow control valves 84, one or more sensors 86, and/or various electrical conductors (e.g., wires) and/or fluid passageways, to cite a few possibilities. The housing 72 is also configured to carry one or more connectors of the pod 16 (e.g., one or more of the mechanical or electromechanical connectors described elsewhere above) for coupling or connecting (e.g., fluidly, electrically, etc.) the pod 16 to one or more catheters 14 to facilitate fluid and/or electrical communications or connections between the pod 16 and the port 12, and/or between the pod 16 and one or more other pods 16 of the system 10. In other words, the connector(s) carried by the housing 72 of a given pod 16 may be mated with complementary connector(s) of one or more catheters 14 in order to fluidly and/or electrically connect or couple the pod 16 to the port 12 and/or one or more other pods 16. For example, in the illustrative embodiments shown in FIGS. 10a-13, each pod 16 includes a pair of electromechanical connectors 88 that, in this particular embodiment, comprise female connectors—one (connector 88a) configured to be mated with a complementary electromechanical connector 68 of a first catheter 14, and the other (connector 88b) configured to be mated with a complementary electromechanical connector 68 of a second catheter 14. In any event, and as with the connectors of the catheter(s) 14 and port 12 described above, the connector(s) of the pod(s) 16 may comprise any suitable connectors known in the art as the present disclosure is not intended to be limited to any particular type(s) of connectors or connection techniques for the pod(s) 16.

Turning now to the components housed within the housing 72, the needle assembly 82 generally comprises a needle 90 and an actuation mechanism 92 to move the needle 90 between retracted and deployed states. In at least some implementations, the needle assembly 82 may further include a guide or track 93 (best shown in the illustrative embodiment depicted in FIGS. 12a and 12b) to which the needle 90 may be secured/mounted to and supported by, and along which the needle 90 may travel when moving between the retracted and deployed states. In at least some embodiments, when the needle assembly is in the retracted state, the entire needle assembly 82 is disposed within the housing 72 of the pod 16. Conversely, when in the deployed state, at least a portion of the needle 90 extends through the aperture 80 in the housing 72 so as to engage and puncture the anatomical structure to which fluid is being delivered, thereby allowing fluid to be delivered to that structure. Accordingly, in an embodiment the needle 90 is arranged so as to be axially-aligned with the aperture 80 in the housing 72 to allow the needled to extend through the aperture 80 and into the anatomical structure.

The needle 90 may serve a number of purposes. For one, it may provide a pathway for fluid to pass from the pod 16 and into the anatomical structure to which fluid is being delivered. Accordingly, the needle 90 may be a hollow needle having a channel 94 therein through which fluid supplied to the needle 90 may pass. More particularly, and as will be described more fully below, the pod 12 may include one or more fluid passageways (e.g., tube(s)) 95 that fluidly couple the needle 90 to a connector in the housing 72 that, in turn, is coupled to a catheter 14. The needle 90 may be coupled to a passageway (e.g., passageway 95a) in a number of ways. For example, the end of the passageway 95a may be sized and shaped to receive a portion of the needle 90, which may be inserted into the passageway and held snuggly in place. In other embodiments, a collar overlying both a portion of the passageway 95a and a portion of the needle 90 may be used to couple and hold the passageway 95a and needle 90 together. Accordingly, it will be appreciated that any number of techniques may be used to couple the passageway and needle together, as the present disclosure is not intended to be limited to any particular technique(s). In embodiment, one or more of the fluid passageway(s) 95 (e.g., passageway 95b in FIGS. 10a-12b) may be sufficiently flexible and/or extendable or expandable in an axial direction towards the needle 90 so as to allow the needle 90 to move between the retracted and deployed states. In any event, fluid from one or more fluid lumens 64 in the catheter 14 may flow through the connector to the passageway(s) 95 in the pod 16, and from the passageway(s) 95 to the channel 94 in the needle 90. As will be described below, a valve 84 may be used to control when fluid in the passageway(s) in the pods is ultimately allowed to flow to and/or through the channel 94 in the needle 90, and thus, into the anatomical structure.

The needle 90 of a given pod 16 may also serve a sensing function or purpose. As will be described in greater detail below, the needle 90 may act as a sensing electrode to measure or sense one or more electrical, electrophysiological, or chemical parameters of interest, or parameter(s) that may be used to derive one or more parameter(s) of interest.

For example, in an embodiment, the needle 90 may be used to measure or sense the electrical resistance or impedance in an area or region between two or more pods 16 (e.g., the impedance of a region of the anatomical structure to which fluid is being delivered), to cite just one example. To that end, at least a portion (i.e., the tip) of the needle 90 may be electrically conductive, and may have one or more electrical conductors attached or affixed thereto extending from the needle 90 to an electromechanical connector 88 of the pod 16. When a catheter 14 is electrically connected between that pod 16 and the port 12 via that connector 88, the needle 90 is electrically connected to one or more electrical components in the port 12 and one or more parameter(s) of interest may therefore be measured or sensed.

The actuation mechanism 92 of the needle assembly 82 is operable to cause the needle 90 to move between the retracted and deployed states and, in at least some embodiments, to control the flow of fluid through the needle 90. The actuation mechanism 92 may include a number of components and may be implemented in a number of ways.

Figure 10B:
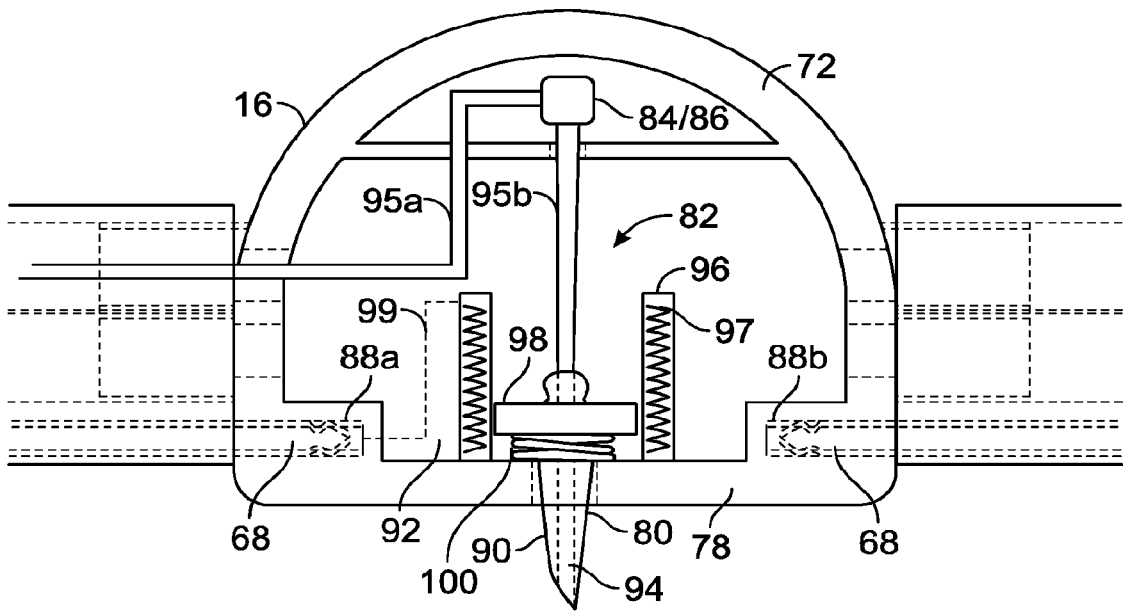

One illustrative way is that illustrated in FIGS. 10a and 10b and involves the use of magnetic fields or forces to actuate the needle assembly 82. More particularly, the actuation mechanism 92 includes one or more electromagnets (e.g., solenoids) 96 disposed at or near the base 78 of the housing 72. As is well known in the art, each electromagnet 96 may include a coil 97 formed of an electrical conductor (e.g., wire) wound around a magnetic core or armature 98 that is movable relative to the coil. The needle 90 is coupled to the armature(s) 98 of the electromagnet(s) 96 such that the needle 90 moves as the armature(s) 98 move. The electromagnet(s) 96, and the coil(s) 97 thereof, in particular, may be electrically connected to a power supply, for example, the power supply 54 in the port 12, via one or more switches and electrical conductors in the port 12, the pod 16 (e.g., conductor(s) 99, and the catheter(s) 14 connecting (directly or indirectly) the port 12 with the pod 16. When the electromagnet(s) 96 is/are energized (i.e., current is applied), a magnetic field is generated that causes the armature(s) 98, and therefore, the needle 90 coupled thereto, to be pulled in an axially-downward direction from the retracted state (FIG. 10a) to the deployed state (FIG. 10b). The actuation mechanism 92 further includes one or more springs 100 to bias the needle 90 and to cause it to retract once the electromagnet(s) 96 is/are de-energized. In the embodiment illustrated in FIGS. 10a and 10b, the spring 100 circumscribes the needle 90; though other suitable spring arrangements may certainly be used instead. In an embodiment, the electromagnet(s) 96 may be selectively energized using one or more of switches disposed between the coils and the power source 54 in the port 12. The switch or switches may be disposed within the port 12 (e.g., one or more of the switches 60 in the port 12) and/or the housing 72 of the pod 16, and may be controlled by the ECU 52 disposed in the port 12. Accordingly, when it is determined that an injection of fluid is needed at the location of the anatomical structure that corresponds to a particular pod 16, the ECU 52 causes the switch or switches corresponding to that pod 16 to close, thereby causing the electromagnet(s) 96 to be energized and a magnetic field having a magnitude sufficient to overcome the bias of the spring 98 to be generated. As the needle 90 is pulled in an axially-downward direction toward the base of the housing 72 (i.e., towards the anatomical structure), the spring 100 compresses. When it is subsequently determined that the needle 90 is to be retracted, the ECU 52 may cause the appropriate switch(es) to open, thereby de-energizing the electromagnet(s) 96. The de-energizing of the electromagnet(s) 96 results in the removal of or reduction in the magnetic field such that the spring 100 expands thereby causing the needle 90 to retract back to the retracted state.

Figure 11A:
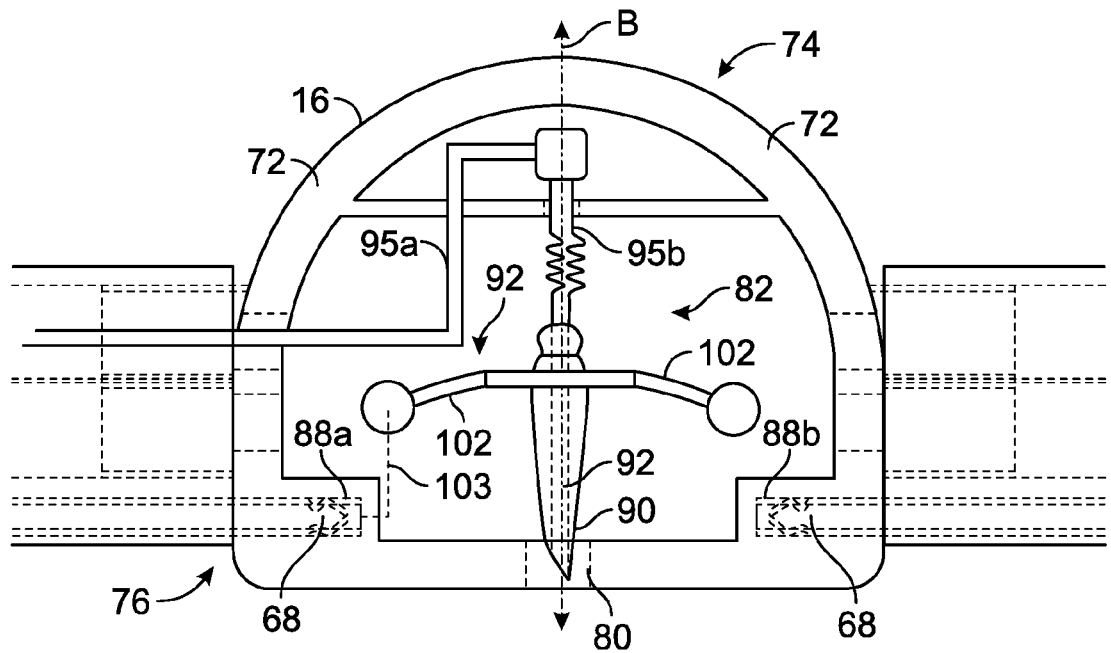
FIGS. 11a and 11b are diagrammatic and side elevation views of another illustrative embodiment of a pod of the fluid delivery system illustrated in FIG. 1, with the needle assembly thereof in a retracted state and a deployed state, respectively.
Figure 11B:
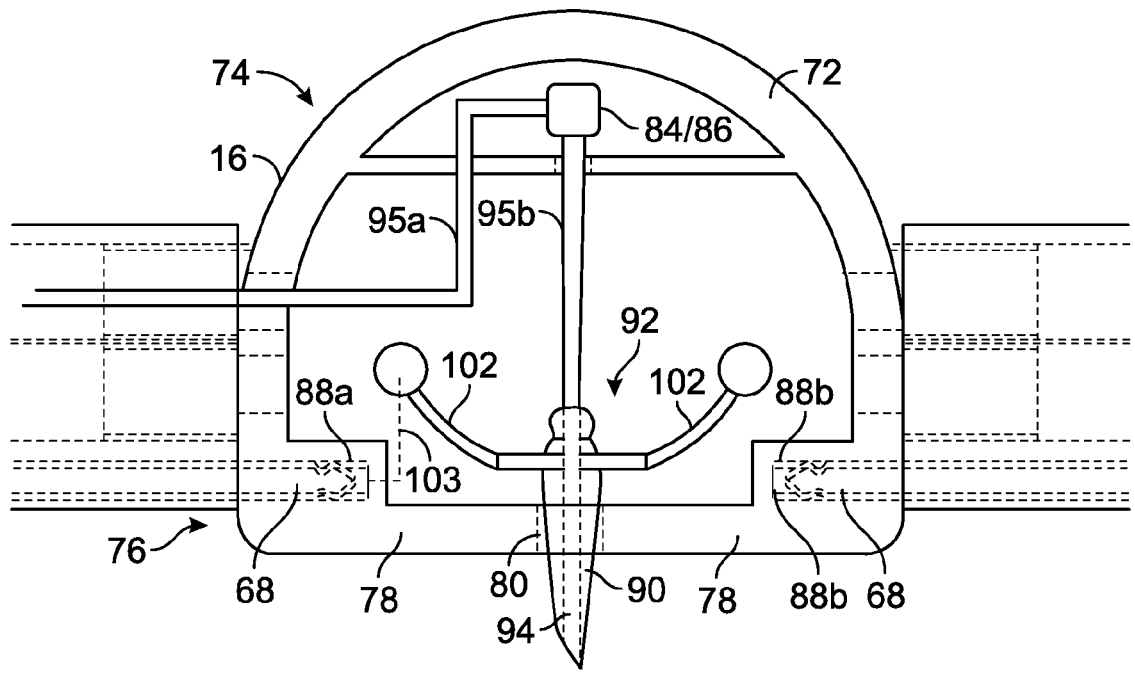

Another way in which the actuation mechanism 92 may be implemented is that illustrated in FIGS. 11*a* and 11*b* and involves the use of piezoelectric elements to actuate the needle assembly 82. More particularly, the actuation mechanism 92 includes one or more piezoelectric elements 102 carried within the housing 72 of the pod 16 that may be selectively electrically connected to, for example, the power supply 54 in the port 12 via one or more switches and electrical conductors in the port 12, the pod 16 (e.g., conductor(s) 103), and the catheter(s) 14 connecting (directly or indirectly) the port 12 with the pod 16. As is known in the art, when electric current is supplied to the piezoelectric element(s) 102, the element(s) 102 deform(s). This deformation causes the needle 90 coupled to the piezoelectric element(s) 102 to be pushed in an axially-downward direction from the retracted state (FIG. 11*a*) to the deployed state (FIG. 11*b*). When the current is subsequently removed, the piezoelectric element(s) 102 revert back to their original state and the needle 90 moves back to the retracted state. In an embodiment, current may be selectively applied to the piezoelectric element(s) 102 using one or more of switches disposed between the piezoelectric element(s) 102 and the power source 54 in the port 12. The switch or switches may be disposed within the port 12 (e.g., one or more of the switches 60 in the port 12) and/or the housing 72 of the pod 16, and may be controlled by the ECU 52 disposed in the port 12. Accordingly, when it is determined that an injection of fluid is needed at the location of the anatomical structure that corresponds to a particular pod 16, the ECU 52 causes the switch or switches corresponding to that pod 16 to close, thereby causing current to be applied to the piezoelectric element(s) 102. As the piezoelectric element(s) 102 deform, the needle 90 is pushed in an axially-downward direction toward base of the house 72 (i.e., towards the anatomical structure). When it is subsequently determined that the needle 90 is to be retracted, the ECU 52 may cause the appropriate switch(es) to open to remove the current from the piezoelectric element(s) 102, thereby causing the piezoelectric element(s) 102 to revert back to it/their original state and causing the needle 90 to retract back to the retracted state.

Yet another way in which the actuation mechanism 92 may be implemented is that illustrated in FIGS. 12*a* and 12*b* and involves the use of pressure to actuate the needle assembly 82, and thus may be considered to be a hydraulic actuation mechanism. More particularly, as fluid is supplied to the pod 16 and flows to the channel 94 of the needle 90, the pressure of the fluid may cause the needle 90 to be pushed in an axially-downward direction from the retracted state (FIG. 12*a*) to the deployed state (FIG. 12*b*) along the track 93, which, in this embodiment, may comprise one or more hydraulic rams. The pressure that causes the needle assembly 82 to actuate may be that of the fluid itself (e.g., when a certain amount of fluid has flowed to the needle 90, the pressure applied to the needle assembly by the fluid causes the needle 90 to move downwardly), may be the pressure applied to the fluid by a physician/clinician who is infusing the port 12 with the fluid (e.g., the pressure applied via the plunger of a syringe used to infuse the port 12), or a combination of both. Once the needle 90 has been deployed and the desired amount of fluid has been injected into the anatomical structure, the pressure lessens and the needle 90 moves back to the retracted state. In an embodiment, the hydraulic rams may include one or more springs or other resilient elements to facilitate the movement of the needle 90 back to the retracted state, much like the spring 100 in the embodiment illustrated in FIGS. 10*a* and 10*b*. In any event, in the illustrative implementation, the actuation mechanism 92 comprises the needle 90 and the track 93 of the needle assembly 82.

While certain particular ways in which the needle actuation mechanism 92 may be implemented have been described above, it will be appreciated that any suitable implementation may be used as the needle actuation mechanism 92 is not limited to any particular implementation(s).

As mentioned above and shown in FIGS. 10*a*-14, in at least some embodiments the pod 16 includes one or more valves 84 and/or one or more sensors 86. The valve(s) 84 and/or sensor(s) 86 are housed within the housing 72 and may be used in the control and/or monitoring of fluid flowing through the pod 16. The valve(s) 84 and/or sensor(s) may comprise constituent components, for example, the needle assembly 82 (and the actuation mechanism 92 thereof, in particular) or may be separate and distinct from other components of the pod 16. In either instance, the valve(s) 84 and/or sensor(s) 86 may be necessary in embodiments wherein the needle 90 may be deployed without delivering fluid to the anatomical structure. For example, in an embodiment wherein the needle 90 serves a sensing function, it may be desirable for the needle to be deployed and to puncture the anatomical structure, but it may not be desirable for the needle 90 to also deliver fluid to the structure while the sensing function is being performed. Such components may also be necessary in embodiments wherein a particular amount of fluid (dosage) is being delivered to the anatomical structure. For example, it may be desirable to stop the delivery of fluid once a particular amount has been delivered.

To that end, and with reference to FIG. 13, for example, a valve 84 may be disposed anywhere in the fluid path between the catheter 14 that supplies fluid to the pod 16 and the needle 90. In an embodiment, such as, for example, that illustrated in FIG. 13 (and those illustrated FIGS. 10*a*-12*b*), the valve 84 may be coupled between two fluid passageways 95 (i.e., 95*a* and 95*b*) in the pod 16 and configured to selectively allow fluid to flow therebetween. The valve 84 may be an electrically controlled valve that may be selectively coupled to, for example, the power source 54 of the port 12 by one or more switches (e.g., one or more switches 60 disposed in the port 12), which, in turn, may be selectively controlled by the ECU 52 housed in the port 12. Accordingly, in an embodiment, the valve 84 may be coupled to electrical components in the port 12 through one or more electrical conductors of one or more catheter(s) 14 that connect, directly or indirectly, the port 12 to the pod 16, and one or more electrical conductors 104 in the pod 16 that electrically connect the valve 84 to the conductor(s) of the one or more catheters 14 (e.g., electrical conductor(s) extending from the valve 84 to an electromechanical connector 88 of the pod 16 that is configured to be electrically connected to electrical conductor(s) of a catheter 14 that, in turn, is connected to the port 12). The valve 84 may comprise any suitable valve known in the art that is configured for use in controlling the flow of fluid as the present disclosure is not intended to be limited to any particular type of valve.

Like the valve 84, the flow sensor 86 may also be disposed anywhere in the fluid path between the catheter 14 that supplies fluid to the pod 16 and the needle 90, and may preferably be disposed between the valve 84 in the pod 16 and the needle 90. Readings from the sensor 86 may be communicated back to the electronics in the port 12 (e.g., ECU 52) and used for a variety of purposes, including, but not limited to, those described herein. Depending on the implementation, the readings may be communicated wirelessly or over one or more electrical conductors. In the latter instance, the sensor 86 may be coupled to the appropriate electronics in the port 12 through, for example, one or more electrical conductors of one or more catheter(s) 14 that connect, directly or indirectly, the port 12 to the pod 16, and one or more electrical conductors 105 in the pod 16 that electrically connect the sensor 86 to the conductor(s) of the one or more catheters 14 (e.g., one or more electrical conductors extending from the sensor 86 to an electromechanical connector 88 of the pod that is configured to be connected to electrical conductors of a catheter 14 that, in turn, is connected to the port 12). Readings from the sensors may be used to determine that fluid is, in fact, flowing to the pod and/or through the needle 90 thereof, and/or to determine how much fluid has flowed therethrough. As will be described below, these readings may then be used in the control the valve(s) 84 in the pod 16. For example, the ECU 52 in the port 12 may be configured to use readings from the sensor 86 to monitor the amount of fluid that has been delivered to the anatomical structure by that pod 16. When the sensed amount of fluid reaches a predetermined threshold programmed into the memory of the ECU 52, the ECU 52 may cause the valve(s) 84 of that pod 16 to close, thereby preventing the further delivery of fluid to the anatomical structure. In another embodiment, readings from the sensor 86 may be used to determine when to deploy the needle 90. More particularly, upon the receipt of readings from the flow sensor 86 indicative of fluid reaching the pod 12/needle 90, the ECU 52 may cause the needle 90 to be deployed so that the fluid can then be delivered to the anatomical structure. These are, of course, only a few examples of how readings from a flow sensor 86 may be used, and it will be appreciated that flow sensor readings may be used for any number of additional or alternate reasons or purposes. It will be further appreciated that the pod 16 may include one or more flow sensors 86 to monitor the flow of fluid through different areas of the pod 16, and that the sensor(s) 86 may comprise any suitable flow sensor known in the art that is configured to measure or sense the fluid flow.

In addition to the fluid passageways/pathways and electrical conductors already described above, in certain embodiments or implementations, a given pod 16 may include any number of additional fluid pathways and/or electrical conductors. More particularly, in an instance wherein the system 10 includes two or more pods 16, one or more of the pods 16 may include one or more fluid pathways 106 and/or one or more electrical conductors 108 extending therethrough to allow downstream pod(s) 16 to be operatively coupled or connected to the port 12 so as to facilitate fluid communication and/or electrical connections between the downstream pod(s) 16 and the port 12. In such an embodiment, these "additional" fluid pathway(s) 106 and/or electrical conductors 108 may extend between connectors (e.g., mechanical and/or electromechanical connectors) in the housing 72 that are configured to be coupled or connected to respective catheters 14, thereby bypassing any of the other components of the pod 16 described above (e.g., the needle assembly 82).

To better illustrate, FIG. 14 illustrates an embodiment of the system 10 wherein the system includes four (4) pods 16 (i.e., 16a-16d). In this embodiment, the pod 16a (which is also illustrated in FIG. 13) is connected or coupled to the port 12 via the catheter 14a and to the pod 16b via the catheter 14b. The pod 16a includes the fluid pathway 95 that allows fluid from a lumen 64 in the catheter 14a to be communicated to the needle assembly 82 of the pod 16a. Because there are three (3) pods downstream of the pod 16a, the pod 16a also includes three (3) additional fluid pathways 106a-106c, each one corresponding to a respective one of the downstream pods 16b-16d. Accordingly, each of the pathways 106a-106c extend from the connector of the pod 16a that is mated with the catheter 14a, to the connector of the pod 16a that is mated with the catheter 14b. The connector coupling the pod 16a with the catheter 14b is configured to allow fluid to flow from the pathways 106a-106c in the pod 16a to one or more fluid lumens 64 in the catheter 14b. In at least some embodiments, the pod 16a may also include electrical conductors to electrically connect electrical conductors in the catheter 14a (and therefore, electrical components of the port 12) to one or more components in the pod 16a (e.g., the valve 84, the sensor 86, etc.). The pod 16a would also include electrical conductors 108 to allow each of the downstream pods 16b-16d to be electrically connected to the port 12. Accordingly, the pod 16a may include electrical conductors 108 that extend from the electromechanical connector 88a of the pod 16a that is mated with the catheter 14a (and a connector 68 thereof, in particular) to the electromechanical connector 88b of the pod 16a that is mated with the catheter 14b (and a connector 68 thereof, in particular). The connector 88b is configured to electrically connect the relevant conductors 108 in the pod 16a to electrical conductor(s) in the catheter 14b which, as shown in FIG. 14, couples pods 16a and 16b together.

As shown in FIG. 14, the pod 16b is connected or coupled to the pod 16a via the catheter 14b, and to the pod 16c via the catheter 14c. As with the pod 16a, the pod 16b includes the fluid pathway 95 that allows fluid from a lumen 64 in the catheter 14b (that passed through the pod 16a) to be communicated to the needle assembly 82 of the pod 16b. Because there are two (2) pods downstream of the pod 16b, the pod 16b also includes two (2) additional fluid pathways 106b and 106c, each one corresponding to a respective one of the downstream pods 16c and 16d. Accordingly, each of the pathways 106b, 106c extend from the connector of the pod 16b that is mated with the catheter 14b, to the connector of the pod 16b that is mated with the catheter 14c. The connector coupling the pod 16b with the catheter 14c is configured to allow fluid to flow from the pathways 106b, 106c in the pod 16b to one or more fluid lumens 64 in the catheter 14c. In at least some embodiments, the pod 16b would also include electrical conductors to electrically connect electrical conductors in the catheter 14b (and indirectly the electronics in the port 12) to one or more components in the pod 16b (e.g., the valve 84, the sensor 86, etc.). The pod 16b would also include electrical conductors 108 to allow each of the downstream pods 16c and 16d to be electrically connected to the port 12. Accordingly, the pod 16b may include electrical conductors 108 that extend from the electromechanical connector 88a of the pod 16b that is mated with the catheter 14b (and a connector 68 thereof, in particular) to the electromechanical connector 88b of the pod 16b that is mated with the catheter 14c (and a connector 68 thereof, in particular). The connector 88b of the pod 16b is configured to electrically connect the relevant conductors in the pod 16b to electrical conductor(s) in the catheter 14c, which, as shown in FIG. 14, couples pods 16b and 16c together As shown in FIG. 11, pods 16c and 16d would be arranged or configured in a substantially similar manner as that described above with respect to pods 16*a* and 16*b*, and therefore, a detailed description of those pods will not be provided.

In addition to the components described above, in at least some embodiments or implementations such as that illustrated in FIG. 1, the system 10 may further include the interrogator or base station 18 briefly described above. The interrogator 18 is configured for wireless communication with the electronics in the port 12, and the ECU 52 thereof, in particular. More specifically, electrical signals may be passed between the interrogator 18 and the ECU 52 through the transmitter/receiver 56 housed in the port 12 and electrically connected to the ECU 52. This communication may be over any number of known communication networks or links using any number of known communication protocols (e.g., personal area networks (PAN), wireless local area network (WLAN), IEEE 802.11, Wi-Fi, WiMax, etc.).

The interrogator 18 may be utilized by a user (e.g., physician or clinician) for a number of purposes. For example, the user may use the interrogator 18 to command the delivery of fluid by one or more of the pods 16 of the system 10. The user may use the interrogator 18 to set or adjust certain operating parameters of the system 10 (e.g., the threshold(s) corresponding to the maximum amount of fluid that is to be delivered 16 to a particular location by a particular pod 16). The interrogator 18 may display the values of one or more parameters (e.g., electrophysiological parameter(s)) that are measured or sensed by the electronics in the port 12 and communicated to the interrogator 18 in order to allow the user to evaluate the efficacy or of the treatment being performed via the fluid delivery, and/or to determine whether adjustments to that treatment are required (e.g., more fluid is required). The user may also use the interrogator 18 to monitor the operation of the pod(s) in the system to ensure that all of the pod(s) 16 are operating in an expected manner.

The interrogator 18 may comprise any number of suitable devices known in the art, and therefore, a detailed description of the structure and operation of the interrogator 18 will not be provided. To summarize, however, the interrogator 18 may include a combination of hardware, software, and/or other components that enable the communication or exchange of information between a user and the system 10, and the electronics in the port 12 thereof, in particular. For example, the interrogator may include an electronic processing device (e.g., a microprocessor, microcontroller, ASIC, etc.), an electronic memory device, and an antenna. The interrogator 18 may further include one or more user interfaces to allow the user to receive information from and/or provide information to, the system 10. The interface(s) may include, for example, and without limitation, a liquid crystal display (LCD), a touch screen LCD, a keypad, a keyboard, a microphone, and/or a speaker, to cite a few possibilities. Again, the present disclosure is not intended to be limited to any particular type of interrogator or other like device, but rather any suitable device may be used.

As at least briefly described above, the system 10 may be configured to perform one or more functions. One obvious function is the delivery of fluid to one or more regions or areas of one or more anatomical structures. For purposes of illustration, one particular way of performing this function will be described below with respect to the embodiment of the system illustrated in FIG. 14; it will be appreciated, however, that other ways may certainly be used in addition to or in lieu of that described below using different embodiments of the system 10.

First, the port 12, catheter(s) 14 (i.e., 14*a*-14*d*), and pods 16 (16*a*-16*d*) are implanted into the body of the patient. Next, the port 12 is infused with the fluid to be delivered to the pods 16 and ultimately injected into the anatomical structure(s) to which the pods 16 are affixed. In an embodiment, this may comprise locating the septum or diaphragm 34 of the port 12 and inserting the needle of a syringe through the septum 34 and into the reservoir 32 of the port. The fluid in the syringe may then be injected into the reservoir 32 by pushing down on a plunger of the syringe. As the fluid fills the reservoir, the pressure applied to the plunger of the syringe causes the fluid to flow equally into the chambers 42*a*-42*d* of the port 12, through the drains 44*a*-44*d* and into respective fluid lumens 64 in the catheter 14*a*, and ultimately into the pods 16*a*-16*d*.

Once the system 10 is loaded with the fluid to be delivered, one or more needle assemblies 82 in the pods 16*a*-16*d* are actuated to deliver the fluid to the anatomical structure. In an embodiment, this comprises the ECU 52 in the port 12 determining which of the needle assemblies 82 to actuate, and then causing that or those assemblies to actuate. This determination may be made automatically by the ECU 52, or alternatively may be made in response to a command or input received from the interrogator 18. For purposes of illustration only, assume that it is determined that only the needle assembly 82 of the pod 16*a* is to be actuated. In response to this determination, the ECU 52 may control one or more switches 60 in the port 12 to couple one or more components in the pod 16*a* to the power source 54 in the port 12 to actuate the assembly 82. Depending on the particular implementation, this may comprise, for example, controlling one or more switches 60 to cause the needle assembly 82 to move to the deployed state. This may additionally or alternatively comprise controlling one or more switches 60 to electrically connect the valve 84 in the pod 16*a* to the power source 54, thereby opening the valve 54 to allow fluid to flow through the channel 94 in the needle 90.

In an embodiment, as the fluid flows through the pod 16*a* to the needle 90, readings from the flow sensor 86 may be communicated back to the ECU 52 through conductors and or other components (e.g., switches) in the pod 16*a*, catheter 14*a*, and port 12. When it is determined by the ECU 52 that a particular amount of fluid has been delivered through the needle 90 to the anatomical structure (by, for example, comparing the readings received from the flow sensor 86 to a predetermined threshold value), the ECU 52 may cause the flow of fluid to be stopped and/or the needle 90 to be retracted. This may comprise, for example, controlling the one or more switches 60 that electrically connect(s) one or more components in the pod 16*a* to the power source 54 to disconnect that or those components from the power source 54, thereby causing the needle assembly 82 to move to the retracted state. This may additionally or alternatively comprise controlling the one or more switches 60 that electrically connect the valve 84 in the pod 16*a* to the power source 54 to disconnect the valve 84 from the power source 54, thereby closing the valve 84 to prevent (or at least limit) additional fluid from flowing through the needle 90.

In an embodiment, once the desired amount of fluid has been delivered to the anatomical structure, the system 10 (e.g., port 12, catheter(s) 14, and pod(s) 16) may be flushed and/or primed with saline or another suitable fluid. This may comprise, for example, infusing the port 12 with saline in the same or similar manner as that described immediately above, and then actuating one or more of the needle assemblies 82 of the pods 16*a*-16*d* to flush and/or prime the system 10.

While one particular way of operating the system 10 to deliver fluid to an anatomical structure has been described above, it will be appreciated that the present disclosure is not intended to be limited solely to this particular way. Rather, the system 10 may be operated in any number of other suitable ways, each of which remains within the spirit and scope of the present disclosure. It will be further appreciated that while the description above was primarily with respect to pod 16a, the description also applies to the other pods 16b-16d with equal force.

As briefly described above, another function that the system 10 may perform relates to the sensing or measuring of one or more parameter(s) of interest, or one or more parameter(s) that may be used to derive one or more parameter(s) of interest. For purposes of illustration only, the description below will be with respect to the sensing or measuring of electrical resistance or impedance, and, in an embodiment, the resistance or impedance of an anatomical structure (e.g., tissue or muscle) or particular region thereof (i.e., between two pods), in particular. It will be appreciated, however, that the present disclosure is not intended to be limited solely to the sensing or measuring of impedance; rather any number of parameter(s) may be sensed or measured by the system 10.

Figure 15:
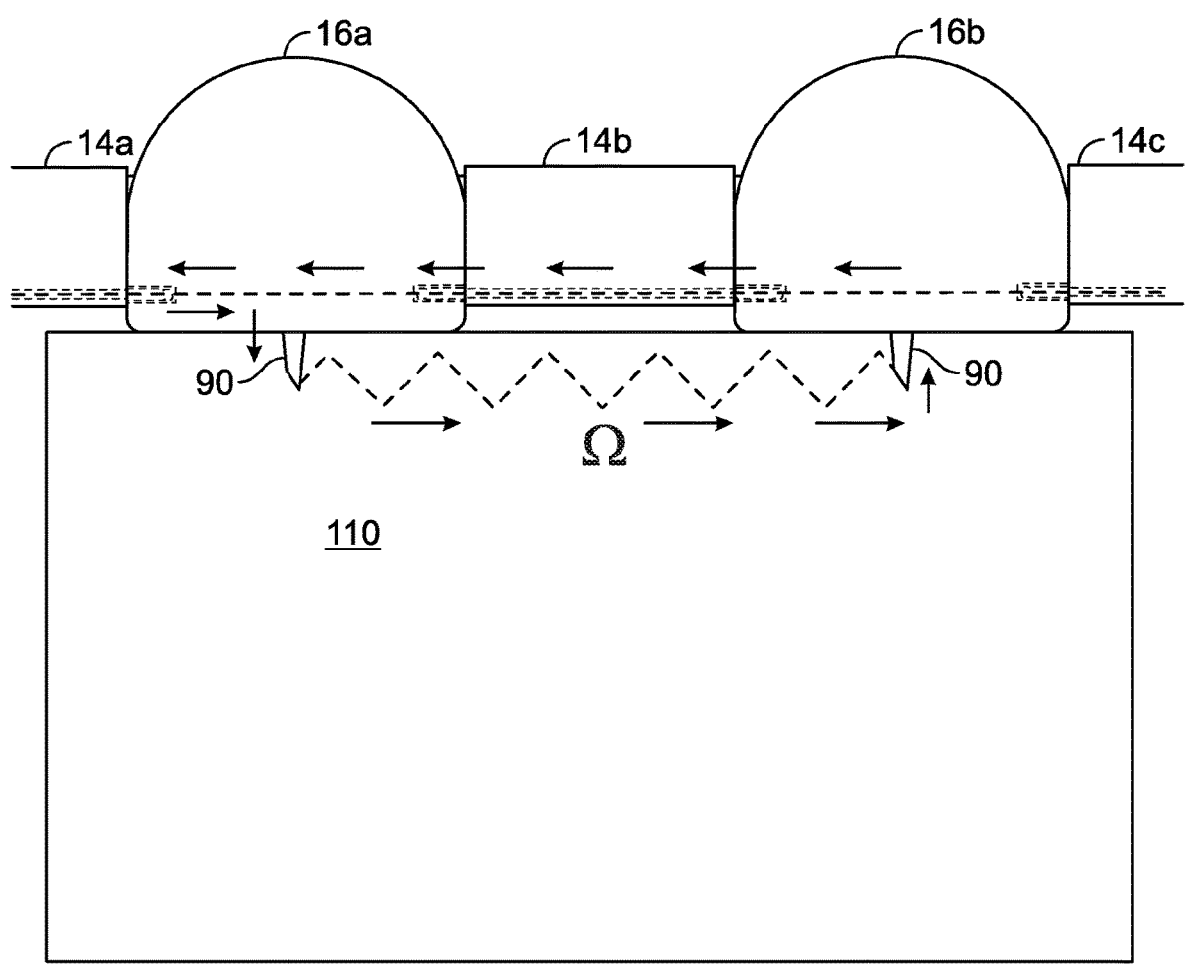
FIG. 15 is a diagrammatic and schematic view of an illustrative way of measuring the impedance of an anatomical structure using an arrangement of pods of the system illustrated in FIG. 1.

In any event, in an instance wherein the system 10 is configured to sense or measure impedance, the system 10 may be configured to do so in a number of ways. One such way is that illustrated in FIG. 15. In this embodiment, the needle 90 of one of the pods 16 (e.g., pod 16a in FIG. 15) is electrically connected to the power source 54 in the port 12 to allow current to flow into the anatomical structure (reference numeral 110 in FIG. 15) when the needle 90 is deployed and penetrates the anatomical structure. The electrical connection between the needle 90 and the power source 54 may be through one or more switches 60 in the port that may be controlled by the ECU 52. The current that flows into the anatomical structure from the needle 90 of the pod 16a flows through the needle(s) 90 of one or more other pods 16 (e.g., pod 16b in FIG. 15) when that or those needles 90 are deployed and penetrate(s) the anatomical structure. The current then flows back to one or more components in the port 12 (e.g., the ohmmeter 58 or ECU 52) that the needle(s) 90 are electrically connected to where it is used to measure or calculate the impedance of at least a portion of the anatomical structure extending between the two needles 90. The electrical connection between the needle 90 of the pod 16b and the electronics of in the port 12 may be facilitated through one or more switches 60 in the port 12 that may be controlled by the ECU 52. The current path described above is represented in FIG. 15 by arrows.

In embodiment, only the needle 90 of one pod 16 (e.g., pod 16a) may be selectively electrically connected to the power source 54 as described above, and only the needle 90 of another pod 16 (e.g., pod 16b) may be selective electrically connected to the component(s) of the port 12 that measure/calculate the impedance. In other embodiments, however, the needles 90 of multiple pods 16 may be configured to be individually selectively electrically connected to the power source 54, components of the port 12 for measuring/calculating impedance, or both. In the latter instance, impedance measurements of different regions of the anatomical structure may be made using different pod combinations to make the necessary measurements. In any event, the electrical connections between the power source 54 or other components in the port 12 and the needles 90 of one or more pods 16 may be facilitated by one or more switches 60 that may be controlled by the ECU 52 to couple the power source 54 and/or impedance measuring/calculating components to the appropriate needles 90, and electrical conductors disposed within the pods 16, catheter(s) 14, and the port 12.

Impedance measurements may be used for a variety of purposes. These measurements may be used by a physician or clinician to evaluate the anatomical structure being treated in order to determine if and/or how much fluid should be delivered to the structure or a particular region thereof. By way of illustration, in an embodiment wherein botox is the fluid being delivered to one or more particular regions of an anatomical structure, the resistance or impedance of that or those regions may be measured in the manner described above and used to determine or evaluate the relaxation or paralysis/blockage state of the region, which, in turn, may then dictate whether or not and/or how much botox should be delivered. Accordingly, the impedance of one or more regions of the anatomical structure may be measured and the measured value may then be used by the ECU 52 to automatically make the necessary determinations as to if botox should be delivered, and if so, how much (e.g., by looking up the measured value in a look-up table or other data structure that correlates impedance with empirically derived botox dosages and/or indications of whether botox delivery is needed), or the value(s) may be communicated to, and displayed, at the interrogator 18 for a physician or clinician to view and then, if appropriate, provide commands to the ECU 52 to cause botox to be delivered to one or more regions using one or more pods 16.

Impedance measurements may additionally or alternatively be used to evaluate the operation of the pods 16, and more particularly, to evaluate whether the needle assemblies 82 thereof are operating (e.g., deploying) properly or in expected manner. For example, impedance may be measured in the manner described above and the measured value may be evaluated to determine whether or not the needle assemblies 82 of one or more of the pods 16 have deployed properly. More particularly, if an impedance measurement is made that exceeds (or, in an embodiment, meets or exceeds) a predetermined threshold or is outside of a predefined range (i.e., is too high to be the impedance of an anatomical structure), then it may be determined that one or more of the needles 90 of the needle assemblies 82 of two or more pods 16 is not in contact with the anatomical structure but rather is in "air," and thus, did not deploy properly. Measures may then be taken to address the functionality and operation of that or those particular pod(s) 16.

Accordingly, it will be appreciated that impedance measurements made by the system 10 may be used for a variety of purposes, including, but not limited to, those described above.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A fluid delivery system for delivering fluid to an anatomical structure of a patient, comprising:
   a port having a fluid reservoir and a port connector in fluid communication with the fluid reservoir;
   a first implantable pod having a needle assembly comprising:
      a hollow needle, and
      a needle actuation mechanism to move the needle between a retracted state and a deployed state, and a pod connector in fluid communication with the needle assembly; and
   a first catheter comprising:
      a shaft having a first end, a second end opposite the first end, and at least one fluid lumen disposed therein extending between the first and second ends,
      a first connector disposed at the first end of the shaft, and
      a second connector disposed at the second end of the shaft;
   a second implantable pod having a needle assembly comprising a hollow needle, and a needle actuation mechanism to move the needle between a retracted state and a deployed state, and a pod connector in fluid communication with the needle assembly of the second implantable pod; and
   a second catheter comprising a shaft having a first end with a first connector, a second end with a second connector opposite the first end, and at least one fluid lumen disposed therein extending between the first and second ends of the second catheter;
   wherein one of the first and second connectors of the first catheter is to be mated with the port connector, and the other of the first and second connectors of the first catheter is to be mated with the pod connector of the first pod so as to at least fluidly couple the port to the first pod; and
   wherein one of the first and second connectors of the second catheter is to be mated with a fluid pathway of the first pod, and the other of the first and second connectors of the second catheter is to be mated with the pod connector of the second pod so as to at least fluidly couple the first and second pods.

2. The fluid delivery system of claim 1 wherein the port further comprises:
   a body including an opening at one end thereof, and having disposed therein: the fluid reservoir, a chamber, a fluid passageway to fluidly couple the fluid reservoir with the chamber, and a drain in fluid communication with the chamber; and
   a septum carried by the body and extending across and overlaying the opening of the body, the septum being penetrable by a needle to inject fluid into the fluid reservoir;
   wherein the port connector is carried by the body and fluidly coupled to the chamber by the drain.

3. The fluid delivery system of claim 2, wherein the fluid passageway of the port comprises a one-way valve to allow fluid in the reservoir to flow to the chamber, and to prevent fluid in the chamber from flowing into the reservoir.

4. The fluid delivery system of claim 1 wherein the first pod further comprises:
   a housing including a base having an aperture therein, the needle assembly disposed within the housing; and
   one or more fluid passageways disposed within the housing to fluidly couple the pod connector of the first pod to the needle assembly;
   wherein, when the needle actuation mechanism of the first pod is in the deployed state, at least a portion of the needle of the first pod extends through the aperture in the base of the housing.

5. The fluid delivery system of claim 4 wherein, when the needle actuation mechanism of the first pod is in the retracted state, the entire needle assembly of the first pod is disposed within the housing of the first pod.

6. The fluid delivery system of claim 1 wherein the pod is a first pod, the fluid delivery system further comprising:
   a third implantable pod having a needle assembly comprising a hollow needle, and a needle actuation mechanism to move the needle between a retracted state and a deployed state, and a pod connector in fluid communication with the needle assembly of the third implantable pod; and
   wherein the first catheter has a third connector to be mated with the pod connector of the third pod so as to at least fluidly couple the port to the third pod.

7. The fluid delivery system of claim 1 wherein the first catheter has an electrical conductor supported by the shaft and extending between the first and second ends, the electrical conductor to mate with the port and the first pod.

8. The fluid delivery system of claim 7 further comprising an electronic control unit supported by the port;
   wherein a fluid passageway of the first pod comprises a valve and a flow sensor to control fluid flow to the needle of the first pod.

9. The fluid delivery system of claim 7 wherein the second catheter has an electrical conductor supported by the shaft and extending between the first and second ends of the second catheter, the electrical conductor of the second catheter to mate with the first pod and the second pod.

10. The fluid delivery system of claim 7 wherein the port has an electrical connector; and
    wherein the first catheter has a first electrical connector disposed at the first end of the shaft, and a second electrical connector disposed at the second end of the shaft, the first and second electrical connectors electrically connected to the electrical conductor of the first catheter, wherein one of the first and second electrical connectors is to be mated with the port electrical connector.

11. The fluid delivery system of claim 7 wherein the needle of the first pod is a sensing electrode such that the needle is electrically connected to the port via the electrical conductor in the first catheter to measure one or more parameters of interest.

12. The fluid delivery system of claim 11 wherein the needle of the second pod is a sensing electrode and is electrically connected to the port to measure one or more parameters of interest.

13. The fluid delivery system of claim 12 further comprising an electronic control unit supported by the port, and in communication with the needles of the first and second pods, the electronic control unit to measure impedance of at least a portion of the anatomical structure extending between the needles of the first and second pods.

14. The fluid delivery system of claim 1 wherein the needle actuation mechanism of the first pod further comprises an electromagnet solenoid to move the needle of the first pod to the deployed state when activated, and a spring to bias the needle of the first pod towards the retracted state.

15. The fluid delivery system of claim 1 wherein the needle actuation mechanism of the first pod further comprises a piezoelectric element to move the needle of the first pod to one of the deployed and retracted states when current is supplied thereto, and move the needle of the first pod to the other of the deployed and retracted states when current is removed therefrom.

16. The fluid delivery system of claim 1 wherein the port further comprises an electronic control unit in communication with the needle actuation mechanism of the first pod to control a position of the needle of the first pod.

17. The fluid delivery system of claim 16 further comprising a base station for wireless communication between the port and the electronic control unit for use in controlling operation of the fluid delivery system.

18. The fluid delivery system of claim 1 further comprising an electronic control unit supported by the port;
   wherein a fluid path between the first catheter and the needle of the first pod comprises a first valve to control fluid flow to the needle of the first pod;
   wherein a fluid path between the second catheter and the needle of the second pod comprises a second valve to control fluid flow to the needle of the second pod; and
   wherein the electronic control unit is in communication with the first valve to control a position of the first valve, and is in communication with the second valve to control a position of the second valve.

* * * * *